United States Patent
Giulian (12)

(10) Patent No.: US 8,334,100 B2
(45) Date of Patent: *Dec. 18, 2012

(54) METHODS FOR DIAGNOSIS AND MONITORING OF NEUROLOGICAL DISEASE BY DETECTION OF AN EXCEPHALOTOXIN

(75) Inventor: Dana J. Giulian, Houston, TX (US)

(73) Assignee: Jacobus Pharmaceutical Company, Inc., Princeton, NJ (US)

( * ) Notice: Subject to any disclaimer, the term of this patent is extended or adjusted under 35 U.S.C. 154(b) by 225 days.

This patent is subject to a terminal disclaimer.

(21) Appl. No.: 12/727,359

(22) Filed: Mar. 19, 2010

(65) Prior Publication Data

US 2010/0209952 A1  Aug. 19, 2010

Related U.S. Application Data

(63) Continuation of application No. 11/970,587, filed on Jan. 8, 2008, now Pat. No. 7,718,394, which is a continuation of application No. 10/543,486, filed as application No. PCT/US2004/002236 on Jan. 27, 2004, now Pat. No. 7,344,853.

(60) Provisional application No. 60/443,219, filed on Jan. 27, 2003.

(51) Int. Cl.
*C12Q 1/68* (2006.01)
*C12P 19/34* (2006.01)
(52) U.S. Cl. .......................... 435/6.16; 435/5
(58) Field of Classification Search .............. None
See application file for complete search history.

(56) References Cited

U.S. PATENT DOCUMENTS

| | | | |
|---|---|---|---|
| 2,546,658 A | 3/1951 | Surrey | |
| 3,689,671 A | 9/1972 | Johnston et al. | |
| 3,702,362 A | 11/1972 | Shen et al. | |
| 3,715,375 A | 2/1973 | Shen et al. | |
| 3,775,403 A | 11/1973 | Shen et al. | |
| 3,775,444 A | 11/1973 | Jensen et al. | |
| 3,786,050 A | 1/1974 | Shen et al. | |
| 4,338,334 A | 7/1982 | Jensen et al. | |

(Continued)

FOREIGN PATENT DOCUMENTS

WO    WO 2004/066940 A3    8/2004

(Continued)

OTHER PUBLICATIONS

Honda, et al. A manual method for the spectrophotometric determination of reducing carbohydrates with 2-cyanoacetamide. Anal. Biochem. 1982; 119(1):194-199.*

(Continued)

*Primary Examiner* — Zachariah Lucas
*Assistant Examiner* — Stuart W Snyder
(74) *Attorney, Agent, or Firm* — Woodcock Washburn, LLP

(57) ABSTRACT

Encephalotoxin produced by activated mononuclear phagocytes is present in individuals having neurological disease including neurodegenerative and neuro-inflammatory diseases, such as Alzheimer's disease (AD), HIV-1-associated dementia (HAD), Creutzfeldt-Jakob disease, Mild Cognitive Impairment, prion disease, minor cognitive/motor dysfunction, acute stroke, acute trauma, or neuro-AIDS. Biochemical detection of encephalotoxin according to the methods of the invention will allow diagnosis of neurological disease in early, presymptomatic stages, thereby allowing early intervention in disease progression as well as identification of subjects or populations at risk for developing neurodegenerative disease. The methods of the invention also provide a mechanism for monitoring progression and treatment of neurological disease.

23 Claims, 19 Drawing Sheets

U.S. PATENT DOCUMENTS

| | | | |
|---|---|---|---|
| 5,532,219 A | 7/1996 | McGeer | |
| 6,043,283 A | 3/2000 | Giulian | |
| 6,071,493 A | 6/2000 | Giulian | |
| 6,451,544 B2 | 9/2002 | Giulian | |
| 6,475,742 B2 | 11/2002 | Giulian | |
| 6,475,745 B1 | 11/2002 | Giulian | |
| 7,344,853 B2 * | 3/2008 | Giulian | 435/29 |
| 7,718,394 B2 * | 5/2010 | Giulian | 435/29 |
| 2001/0016326 A1 | 8/2001 | Giulian | |
| 2001/0016327 A1 | 8/2001 | Giulian | |
| 2002/0198231 A1 | 12/2002 | Nelson | |

FOREIGN PATENT DOCUMENTS

| | | |
|---|---|---|
| WO | WO 2004/066943 A2 | 8/2004 |

OTHER PUBLICATIONS

55 FR 9576, 1990, Part 493.1253, http://www.phppo.cdc.gov/clia/regs/toc.aspx.

Ael et al., "A rating scale for amyotrophic lateral sclerosis: description and preliminary experience", Ann Neurol, 1987, 22, 328-333.

Aisen et al., "Inflammatory mechanisms in Alzheimer's disease: implications for therapy", Am J Psychiatry, 1994, 151, 1105-1113.

Al-Haideri, et al., "Heparan sulfate proteoglycan-mediated uptake of apolipoprotein E-triglyceride-rich lipoprotein particles: a major pathway at physiological particle concentrations", Biochemistry, 1997, 36, 12766-12772.

Anderson et al. "HIV-1-Associated Dementia: A Metabolic Encephalopathy Perpetrated by Virus-Infected and Immune-Competent Mononuclear Phagocytes", Journal of Acquired Immune Deficiency Syndrome, Oct. 1, 2002, S43-S54, 31, Issue No. 1525-4135, Lincott Williams & Wilkins, Philadelphia.

Andreasen et al., "Cerebrospinal fluid beta-amyloid sub (1-42) in Alzheimer disease: differences between early- and late-onset Alzheimer disease and stability during the course of disease", Archives Neurology, 1999, 56(6), 673-680 (attached 1-13).

Andreasen et al., "Sensitivity, specificity, and stability of CSF-tau in AD in a community-based patient sample", Neurology, 1999, 53, 1488-1494.

Appel et al. "A Rating for Amyotrophic lateral sclerosis: Description and preliminary experience", Ann. Neurol., 1987, 22, 328-333.

Asare et al., "Neuronal pattern correlates with severity of human immunodeficiency virus-associated dementia complex", Am J Path, 1996, 148(1), 31-38.

Author Unknown "Anti-Inflammatory drugs for the treatment of Alzheimer's-type dementia", Expert Opinion on Therapeutic Patents, Jan. 1, 1994, 4(10), 1271-1273.

Bales et al., "Lack of apolipoprotein E dramatically reduces amyloid beta-peptide deposition", Nat Genet al. 1997, 17, 263-264.

Bales et al., "Neuroinflammation and Alzheimer's disease: critical roles for cytokine/Abeta-induced glial activation, NF-kaaB, and apolipoprotein E", Neurobiol Aging, 2000, 21, 427-432.

Bame et al., "Abeta(1-40) prevents heparanase-catalyzed degration of heparin sulfate glycosaminoglycans and proteoglycans in vitro a role for heparin sulfate proteoglycan turnover in Alzheimer's disease", J Biol Chem, 1997, 272(27), 17005-17011.

Banati et al., "Cytotoxicity of microglia", Glia, 1993, 7, 111-118.

Barton et al., "Bullous systemic lupus erythematosus: An unusual clinical course and detectable circulating autoantibodies to the epidermolysis bullosa acquisita antigen", Journal of the American Academy of Dermatology, 15(2), Aug. 1, 1986, 369-373.

Becker "The natural history of alzheimer's disease Description of study cohort and accuracy of diagnosis", Archives of Neurology, 1994, 51(6), 3 pages, abstract http://archneur ama-assnorg/cgi/content/abstract/51/6/585, downloaded from the internet on Aug. 14, 2007.

Berg et al., "Clinical demential rating (CDR)", Psychopharmacol Bull, 1988, 24(4), 637-639.

Bigio et al., "Synapse loss is greater in presenile than senile onset Alzheimer disease", Neuropath A Neurobiol, 2002, 28, 218-227.

Bigio et al., "Synapse loss may be a minor contributor to decreased regional cerebral blood flow in Alzheimer disease", Dement Geriatr Cong Disord, 2003, 15, 72-78.

Bischkopf et al., "Mild cognitive impairmentsup1—a review of prevalence, incidence and outcome according to current aroaches", Acta Psychiatr Scand, 2002, 106, 403-414.

Blessed et al.,e association between quantitative measures of dementia and of senile change in the cerebral grey matter of elderly subjects, Br J Psychiat, 1968, 114, 797-811.

Boireau et al., "Thalidomide reduces MPTP-induced decrease in striatal dopamine levels in mice", Neurosci Lett, 1997, 234, 123-126.

Boje et al., "Microglial-produced nitric oxide and reactive nitrogen oxides mediate neuronal cell death", Brain Res, 1992, 587, 250-256.

Bonney et al., "Physiological and pharmacological regulation of prostaglandin and leukotriene production by macrophages", J of Leukocyte Biol, 1984, 35, 1-10.

Bornemann et al., "Transgenic mouse models of Alzheimer's disease", Annu NY Acad Sci, 2000, 908, 260-266.

Borst et al., "New mechanisms of drug resistance in parasitic protozoa", Annul Rev Microbiol, 1995, 49, 427-460.

Breitner et al., "Inverse association of anti-inflammatory treatments and Alzheimer's disease: Initial results of a co-twin control study", Neurology, 1994, 44, 227-232.

Bronfman et al., "No evidence for cholinergic problems in apolipoprotein E knockout and apolipoprotein E4 transgenic mice", Neurosci, 2000, 97(3), 411-417.

Brown "Microglia and prion disease: a review", Histology & Histopathology, 1997, 12, 883-892.

Buttini et al., "Expression of human apolipoprotein E3 or E4 in the brains of apoEsup-/- mice: isoform-specific effects on neurodegeneration", J Neurosci, 1999, 19(2), 4867-4880.

Campbell et al., "Heparan sulfate-degrading enzymes induce modulation of smooth muscle phenotype", Exp Cell Res, 1992, 200, 156-167.

Carlsson et al., "Clinical relevance of the quantification of apolipoprotein E in cerebrospinal fluid", Clin Chim Acta, 1991, 196, 167-176.

Castillo et al., "The sulfate moieties of glycosaminoglycans are critical for the enhancement of beta-amyloid protein fibril formation", J of Neurochen, 1999, 72, 1681-1687.

Chao et al., "Activated microglia mediate neuronal cell injury via a nitric oxide mechanism", J Immunology, 1992, 149, 2736-2741.

Chaudhary et al., "Expression and activity of P-glycoprotein, a multidrug efflux pump, in human hematopoietic stem cells", Cell, 1991, 66, 85-94.

Clemens et al., "Implants containing beta-amyloid protein are not neurotoxic to young and old rat brains", Neurobiol Aging, 1992, 13, 581-586.

Collinge "Prion diseases of humans and animals: their causes and molecular basis", Annu Rev Neurosci, 2001, 24, 519-550.

Colton et al. "Production of superoxide anion by a CNS macrophage, the microglia", FEBS Lett, 1987, 223(2), 284-288.

Corder et al. "Gene dose of apolipoprotein E type 4 allele and the risk of Alzheimer's disease in late onset families", Science, 1993, 261, 921-923.

Corder et al. "HIV-1-infected subjects with the E4 allele for APOE have excess dementia and peripheral neuropathy", Nature Medicine, 1998, 4(10), 1182-1184.

Corder et al. "Protective effect of apolipoprotein E type 2 allele for late onset Alzheimer disease", Nat Genet al. 1994, 7, 180-183.

Cotman et al. "Agrin binds to beta-amyloid (Abeta), accelerates Abeta fibril formation and is localized to Abetadeposits in Alzheimer's disease brain", Mol Cell Neurosci, 2000, 15, 183-198.

Cotman et al. "Beta-amyloid neurotoxicity: a discussion of in vitro findings", Neurobiol Aging, 1992, 13, 587-590.

D'Agostino et al. "A suggestion for using powerful and informative tests of normality", Amer Statist, 1990, 44(4), 316-321.

Davis "Neuronal abnormalities, not amyloid, are the cause of dementia in Alzheimer disease", Alzheimer Disease Terry, RD, et al (Eds), 1994, Chapter 19, 327-333.

Davis et al. "Anti-thy-1 immunotoxin, OX-7-saporin, destroys cerebellar Purkinje cells after intraventricular injection in rats", Brain Res, 1989, 504, 216-222.

De Luca et al. "Correlates of independent HIV-1 replication in the CNS and of its control by antiretrovirals", Neurology, 2002, 59, 342-347.

DeKosky et al. "Looking backward to move forward: early detection of neurodegenerative disorders", Science, 2003, 302, 830-834.

Delacourte "General and dramatic glial reaction in Alzheimer brains", Neurology, 1990, 40, 33-37.

Delaere et al. "Subtypes and differential laminar distributions of betaA4 deposits in Alzheimer's disease: relationship with the intellectual status of 26 cases", Acta Neuropathol, 1991, 81, 328-335.

Denis "Human monocytes/macrophages: NO or no NO?", J of Leukoc Biol, 1994, 55, 682-684.

Dickson et al. "Neuroimmunology of Alzheimer's disease: a conference report", Neurobiol of Aging, 1992, 13, 793-798.

Diggle "An approach to the analysis of repeated measurements", Biometrics, 1988, 44, 959-971.

Dore et al. "Changes to AIDS dementia complex in the era of highly active antiretroviral therapy", AIDS, 1999, 13, 1249-1253.

Dunzendorfer "Effects of thalidomide on neutrophil respiratory burst chemotaxis, and transmigration of cytokine- and endotoxin-activated endothelium", Naunym-Schmiedeb Arch Pharm, 1997, 356, 529-535.

Duyckaert et al. "Does amyloid precede paired helical filaments in the senile plaque? A study of 15 cases with graded intellectual status in aging and Alzheimer disease", Neurosci Lett, 1988, 91, 354-359.

Egensperger et al. "Microglial activation in Alzheimer's disease: association with APOE genotype", Brain Path, 1998, 8, 439-447.

Eikelenboom et al. "Inflammatory mechanisms in Alzheimer's disease", TIPS, 1994, 15, 447-450.

Eikelenboom et al. "Neuroinflammation in alzheimer's disease and disease", GLIA, 2002, 232-239.

Elias et al. "The Preclinical phase of Alzheimer's disease", Arch Neurol, 2000, 57, 808-813.

Evans et al. "Oxidative damage in Alzheimer's dementia, and the potential etiopathogenic role of aluminosilicates, microglia and micronutrient interactions", Free Radicals and Aging, 1992, 62, 178-189.

Everall et al. "A review of neuronal damage in human immunodeficiency virus infection: its assessment, possible mechanism and relationship to dementia", J of Neuropath & Exp Neurol, 1993, 52(6), 561-566.

Farrer et al. "Effects of age, sex, and ethnicity on the association between apolipoprotein E genotype and Alzheimer disease a meta-analysis", JAMA, 1997, 278(16), 1349-1356.

Feyzi et al. "Characterization of heparin and heparan sulfate domains binding to the long splice variant of platelet-derived growth factor a chain", J Biol Chem, 1997, 272(9), 5518-5524.

Fleisher et al. "Clinical predictors of progression to Alzheimer disease in amnestic mild cognitive impairment", Neurology, 2007, 68, 1588-1595, abstract, 2 pages, http://wwwneurologyorg/cgi/content/abstract/68/19/1588, downloaded from the internet on Aug. 15, 2007.

Flicker et al. "Mild cognitive impairment in the elderly: predictors of dementia", Neurology, 1991, 41, 1006-1009.

Fogelman et al. "Modification of recalde method for the isolation of human monocytes", J of Lipid Res, 1988, 29, 1243-1247.

Fowler et al., "Report on chloroquine and dapsone in the treatment of rheumatoid arthritis: a 6-month comparative study", Annals of the Rheumatic Diseases, 43, 1984, 200-204.

Freeman et al. "Human platelet heparanase: purification, characterization, and catalytic activity", Biochem J, 1998, 330, 1341-1350.

Frei et al. "Antigen presentation and tumor cytotoxicity by interferon-gammatreated microglial cells", Eur J Immunol, 1987, 17, 1271-1278.

Fukuchi et al. "Alzheimer's disease and heparan sulfate proteoglycan", Front Biosci, 1998, 21, 327-337 (abstract).

Funahashi et al. "Association of apolipoprotein E with the low density lipoprotein receptor: demonstration of its cooperativity on lipid microemulsion particles", J Biochem, 1989, 105, 582-587.

Games et al. "Alzheimer-type neuropathology in transgenic mice over expressing V717Fbeta-amyloid precursor protein", Nature, 1995, 373, 523-527.

Games et al. "Lack of Alzheimer pathology after beta-amyloid protein injections in rat brain", Neurobiol of Aging, 1992, 13, 569-576.

Gatti et al. "Penetration of dapsone into cerebrospinal fluid of patients with AIDS", J Antimicro Chemotherap, 1997, 40, 113-115.

Ghiselli et al. "Foam cell conversion of macrophages alters the biosynthesis of heparan sulfate", Biochem Biophys Res Commun, 1998, 247, 790-795.

Giulian et al. "The HHQK domain of beta-amyloid provides a structural basis for the immunopathology of Alzheimer's disease", J Biol Chem, 1998, 273(45), 29719-29726.

Giulian "A strategy for identifying immunosuressive therapies for Alzheimer's disease", Alzheimer's Disease and Associated Disorders, 1998, 12(Sul 2), S7-S14.

Giulian "Glia mediated brain injury in Alzheimers disease", Baylor Institute of Medicine, National Institute of Aging, 1998, Grant No. 5R01AG012548-03, 2 pages (Abstract).

Giulian "Microglia and diseases of the nervous system", Curr Topics Neurol, 1992, 12, 23-54.

Giulian "Microglia and neuron dysfunction", Neuroglia, Oxford Univ Press, Kettenmann, H, et al (Eds), 1995, 671-684.

Giulian "Microglia and the immune pathology of Alzheimer disease", Am J Hum Genet al. 1999, 65, 13-18.

Giulian "Novel CSF biomarker to predict impaired cognition in HIV", Inflame Therapeutics, Inc, National Institute of Neurological Disorders and Stroke, 2004, Grant No. 1R42NS046997-01A1 , 2 pages (Abstract).

Giulian "Reactive glia as rivals for regulating neuronal survival", Glia, 1993, 7, 102-110.

Giulian "Scavenger receptors and CNS", Baylor Institute of Medicine, National Institute of Neurological Disorders and Stroke, 1999, Grant No. 1R01NS035908-01A1 , 2 pages (Abstract).

Giulian "Suressing plaque activation of microglia in alzheimers", Baylor Institute of Medicine, National Institute of Neurological Disorders and Stroke, 1997, Grant No. 1 R01NS035972-01, 2 pages (Abstract).

Giulian et al. "Cell surface morphology identifies microglia as a distinct class of mononuclear phagocytes", J Neurosci, 1995, 15(11), 7712-7726.

Giulian et al. "Characterization of ameboid microglia isolated from developing mammalian brain", J Neurosci, 1986, 6(8), 2163-2178.

Giulian et al. "Inflammatory glia mediate delayed neuronal damage after ischemia in the central nervous system", Stroke, 1993, 24(Sul I), I-84-I-90.

Giulian et al. "Inhibition of mononuclear phagocytes reduces ischemic injury in the spinal cord", Ann Neurol, 1990, 27, 33-42.

Giulian et al. "Microgliosis and impaired cognition", Inflammatory Mechanisms of Neurodegeneration and Its Management, Humana Press, Wood, P (Ed), 1998, 4, 109-128.

Giulian et al. "Neurotoxins from HIV-1 infected mononuclear phagocytes", Neurology of AIDS, Chapman and Hall, Gendelman, H (Eds), 1998, Chapt 8, 117-129.

Giulian et al. "Phagocytic Microglia Release Cytokines and Cytotoxins That Regulate the Survival of Astrocytes and Neurons in Culture", Journal. 1994, 25( 0197-0186), 227-233.

Giulian et al. "Secretion of neurotoxins by mononuclear phagocytes infected with HIV-1", Science, 1990, 250, 1593-1596.

Giulian et al. "Senile plaques stimulate microglia to release a neurotoxin found in Alzheimer brain", Neurochem Int, 1995, 27, 119-137.

Giulian et al. "Specific domains of beta-amyloid from Alzheimer plaque elicit neuron killing in human microglia", J of Neurosci, 1996, 16(19), 6021-6037.

Giulian et al. "Study of receptor-mediated neurotoxins released by HIV-1 infected mononuclear phagocytes found in human brain", J of Neuroscience, 1996, 16(10), 3139-3153.

Giulian et al. "The envelope glycoprotein of human immunodeficiency virus type 1 stimulates release of neurotoxins from monocytes", Proceedings of the National Acad of Sci, 1993, 90, 2769-2773.

Giulian et al. "The impact of microglia-derived cytokines upon gliosis in the CNS", Dev Neurosci, 1994, 16, 128-136.

Giulian et al. "The role of mononuclear phagocytes in wound healing after traumatic injury to adult mammalian brain", J of Neurosci, 1989, 9(12), 4416-4429.

Godavarti et al. "A comparative analysis of the primary sequences and characteristics of heparinases I, II, III from flavobacterium heparinum", Biochem & Biophys Res Comm, 1996, 229, 770-777.

Goldman et al. "Evidence that age-associated memory impairment is not a normal variant of aging", Alz Dis, Assoc Dis, 2001, 15, 72-79.

Goto et al. "Neuronal inputs to hiocampal formation in Alzheimer's disease and in parkinsonism-dementia complex on Guam", Acta Neuropatol, 1990, 79, 545-550.

Griffin et al. "Interleukin-1 expression in different plaque types in Alzheimer's disease: significance in plaque eution", J of Neuropathology & Experimental Neurology,, 1995, 54(2), 276-281.

Grundman et al. "Rate of dementia of Alzheimer type in subjects with mild cognitive impairment; the ADCS cooperative study", Neurology, 1996, 46, 403.

Gutmann et al. "Dapsone motor neuropathy—an axonal disease", Neurology, 1976, 26, 514-516.

Haar et al., "A double-blind comparative study of hydroxychloroquine and dapsone, alone and in combination, in Rheumatoid Arthritis", Scand J Rheumatol, 22, 1993, 113-118.

Halliday al. "Effect of anti-inflammatory medications on neuropathological findings in Alzheimers disease", Arch Neurol, 2000, 57(6), 831-836 ( 1-10 attached).

Hardy et al. "The amyloid hypothesis of Alzheimer's disease: progress and problems on the road to therapeutics", Science, 2002, 297, 353-356.

Harris et al. "beta-amyloid peptide derived, oxygen dependent free radicals inhibit glutamate uptake in cultured astrocytes: implications for Alzheimer's disease", Neuroreport, 1995, 6, 1875-1879.

Hensley et al. "A model for beta-amyloid aggregation and neurotoxicity based on free radical generation by the peptide: relevance to Alzheimer disease", Proc Natl Acad Sci, 1994, 91, 3270-3274.

Heymann et al. "Derivatives of p,p'-diaminodiphenyl sulfone", J of Am Chem Soc, 1945, 67, 1979-1990.

Hof et al. "The Cellular Basis of Cortical Disconnection in Alzheimer Disease and Related Dementing Conditions", Alzheimer Disease, Terry, RD, et al (Eds), Raven Press, NY, 1994, 197-229.

Hoglund et al. "A double-blind study of the sedative effects of the thalidomide enantiomers in humans", J Pharmacokin Biopharm, 1998, 26(4), 363-383.

Holtzman et al. "Apolipoprotein E facilitates neuritic and cerebrovascular plaque formation in an Alzheimer's disease model", Ann Neurol, 2000, 47(6), 739-747.

Holtzman et al. "Apolipoprotein E isoform-dependent amyloid deposition and neuritic degeneration in a mouse model of Alzheimer's disease", Proc Natl Acad Sci USA, 2000, 97(6), 2892-2897.

Hom et al. "Cognitive deficits in asymptomatic first-degree relatives of Alzheimer's disease patients", J Clin Exp Neurol, 1994, 16, 568-576.

Hsiao et al. "Correlative memory deficits, Abeta elevation, and amyloid plaques in transgenic mice", Science, 1996, 274, 99-102.

Hugh et al. "Atypical inflammation in the central nervous system in prion disearse", Current Opinion in Neurology, 2002, 15, 349-354.

Hughes et al. "A new clinical scale for the staging of dementia", Br J of Psychiatry, 1982, 140, 566-572.

Irizarry et al. "AsubSW transgenic mice develop age-related Abeta deposits and neuropil abnormalities but no neuron loss in CA1", J Neuropath Exp Neurol, 1997, 56(9), 965-973.

Ishida et al. "Comparing the anticonvulsive effects of dapsone on amygdala-kindled seizures and hiocampal-kindled seizures in rats", Acta Neurol Scan, 1992, 85, 132-135.

Ishiguro et al. "Phosphorylated tau in human csf is a diagnostic marker for Alzheimer's disease", Neuroscience Letts, 1999, 270, 91-94.

Jemth et al. "Biosynthetic oligosaccharide libraries for the identification of protein binding heapran sulfate motifs Exploring the structural diversity by screening fibroblast growth factor (FGF)1 and FGF2 binding", J Biol Chem, 2002, 277(34), 30567-30573.

Ji et al. "Variable heparan sulfate proteoglycan binding of apolipoprotein E variants may modulate the expression of Type III hyperlipoproteinemia", J Biol Chem, 1994, 269(18), 13421-13428.

Jiang et al. "Glutamate is a Mediator of Neurotoxicity in Secretions of Activated HIV-1-Infected Macrophages",Journal of Neuroimmunology, Jul. 2, 2001, 97-107, 117, Issue No. 0165-5728.

Jordan et al. "Isoform-specific effect of apolipoprotein E on cell survival and beta-amyloid-induced toxicity in rat hiocampal pyramidal neuronal cultures", J Neurosci, 1998, 18(1), 195-204.

Kahle et al. "Combined assignment of tau and neuronal thread protein in Alzheimer's disease CSF", Neurology, 2000, 54(7), 1498-1504.

Kalback et al. "A transgenic mice Tg2576 accumulate Abeta peptides that are distinct from the chemically modified and insoluble peptides deposited in Alzheimer's disease senile plaques", Biochemistry, 2002, 41(3), 922-928.

Kawakami et al. "Reduced immune function and malnutrition in the elderly", Tohoku J Exp Med, 1999, 187, 157-171.

Kayed et al. "Common structure of soluble amyloid oligomers implies common mechanisms of pathogenesis", Science, 2003, 300, 486-489.

Kenyon et al. "Novel sulfhydryl reagents", Methods Enzymol, 1977, 47, 407-430.

Knopman et al. Practice parameter: diagnosis of dementia (an evidence-based review), Neurology, 2001, 56, 1143-1153.

Kobayashi et al. "Reversal of hypercholesterolemia in low density lipoprotein receptor knockout mice by adenovirus-mediated gene transfer of the very low density lipoprotein receptor", J Biol Chem, 1996, 271(12), 6852-6860.

Koh et al. "beta-amyloid protein increases the vulnerability of cultured cortical neurons to excitotoxic damage", Brain Res, 1990, 533, 315-320.

Kosir et al. "Human prostate carcinoma cells produce extracellular heparanases", J Surgical Res, 1997, 67(1), 98-105.

Kreuger et al. "Sequence analysis of heparin sulfate epitopes with graded affinities for fibroblast growth factors 1 and 2", J Biol Chem, 2001, 276(33), 30744-30752.

Kril et al. "Neuron loss from the hiocampus of Alzheimer's disease exceeds extracellular neurofibrillary tangle formation", Acta Neuropathol, 2002, 103, 370-376.

Kuo et al. "Elevated Abeta and apolipoprotein E in Abeta transgenic mice and its relationship to amyloid accumulation in Alzhiemer's disease", Molec Med, 2000, 6(5), 430-439.

LaDu et al. "Purification of apolipoprotein E attenuates isoform-specific binding to beta-amyloid", J Biol Chem, 1995, 270(16) , 9039-9042.

Lamy et al. "Comparison of seven staining methods for senile plaques and neurofibrillary tangles in a prospective series of 15 elderly patients", Neuropathol Al Neurobiol, 1989, 15, 563-578.

Langston "Aging, Neurotoxins and neurodegenerative disease", Aging and the Brain, Raven Press, New York, Terry, RD, 1988, 149-164.

Lawrence et al. "HIV-1 and the brain: connections between HIV-1-associated dementia, neuropathology and neuroimmunology", Microbes Infection, 2002, 4, 301-308.

Leelavathi et al. "Isolation of a Golgi-Rich fraction from rat liver", Biochim Biophys Acta, 1970, 211, 124-138.

Lees "The possible contribution of microglia and macrophages to delayed neuronal death after ischemia", J Neurol Sci, 1993, 114, 119-122.

Levine Biochim Biophys Acta, 1976, 452, 458-467.

Lin et al. "Apolipoprotein E-dependent cholesterol efflux from macrophages: kinetic study and divergent mechanisms for endogenous versus exogenous apolipoprotein E", J Lipid Res, 1999, 40, 1618-1627.

Lindahl et al. "Common binding sites for beta-amyloid fibrils and fibroblast growth factor-2 in heparin sulfate from human cerebral cortex", J Biol Chem, 1999, 274(43), 30631-30635.

Lipton "Prospects for clinically tolerated NMDA antagonists: open-channel blockers and alternative redox states of nitric oxide", TINS, 1993, 16(12), 527-532.

Lipton "Requirement of macrophages in neuronal injury induced by HIV envelope protein gp 120", NeuroReport, 1992, 3(10), 913-915.

Loo et al. "Apoptosis is induced by beta-amyloid in cultured central nervous system neurons", Proc Natl Acad Sci USA, 1993, 90, 7951-7955.

Lucca et al. "Nonsteroidal antiinflammatory drug use in Alzheimer's disease", Biol Psychiatry, 1994, 36, 854-856.

Lyon et al. "Elucidation of the structural features of heparin sulfate important for interaction with the Hep-2 domain of fibronectin", J Biol Chem, 2000, 275(7), 4599-4606.

Maccarana et al. "Minimal sequence in heparin/heparan sulfate required for binding of basic fibroblast growth factor", J Biol Chem, 1994, 268(32), 23898-23905.

Mackenzie et al. "Nonsteroidal anti-inflammatory drug use and Alzheimer-type pathology in aging", Neurology, 1998, 50(4), 986-990.

Mahley "Apolipoprotein E: cholesterol transport protein with expanding role in cell biology", Science, 1988, 240, 622-630.

Mallucci et al. "Update on creutzfeldt-jakob disease", Current Opinion in Neurology, 2004, 17, 641-647.

Mandon et al. "A monomeric protein in the golgi membrane catalyzes both N-deacetylation and N-sulfation of heparan sulfate", J Biol Chem, 1994, 269(16), 11729-11733.

Mann "Neuropathological and neurochemical aspects of Alzheimer's disease", Handbook of Psychopharmacology, Iversen, LL, et al (Eds), Plenum Press, New York, 1988, 1-67.

Masliah "Recent advances in the understanding of the role of synaptic proteins in Alzheimer's disease and other neurodegenerative disorders", J Alzheim Dis, 2001, 3, 121-129.

Masliah et al. "Differential vulnerability of calbindin-immunoreactive neurons in HIV encephalitis", J Neuropath Exp Neurol, 1995, 54(3), 350-357.

Masliah et al. "Diffuse plaques do not accentuate synapse loss in Alzheimer's disease", Am J Pathol, 1990, 137(6), 1293-1297.

Masliah et al. "Selective neuronal vulnerability in HIV encephalitis", J Neuropath Exp Neurol, 1992, 51(6), 585-593.

Masur et al. "Neuropsychological prediction of the dementia and the absence of dementia in healthy elderly persons", Neurology, 1994, 44, 1427-1432.

Mattson et al. "beta-amyloid peptides destabilize calcium homeostasis and render human cortical neurons vulnerable to excitotoxicity", J Neurosci, 1992, 12(2), 376-389.

May et al. "beta-amyloid peptide in vitro toxicity: Lot-to-lot variability", Neurobiol Aging, 1992, 13, 605-607.

Mayeux et al. "Alzheimer's disease genetics: home runs and strikeouts", Ann Neurol, 1998, 44(5), 716-719.

Mayeux et al. "The apolipoprotein epsilon 4 allele in patients with Alzheimer's disease", Ann Neuorol, 1993, 34, 7752-7754.

McChesney "Animal toxicity and pharmacokinetics of hydroxychloroquine sulfate", Am J Med (Sul), 1983, 11-13.

McGeer "Cyclo-oxygenase-2 inhibitors: rationale and therapeutic potential for Alzheimer's disease", Drugs Aging, 2000, 17(1), 1-11.

McGeer et al. "Anti-inflammatory drugs and Alzheimer disease", Lancet al. 1990, 335, 1037.

McGeer et al. "Arthritis and anti-inflammatory agents as possible protective factors for Alzheimer's disease: a review of 17 epidemiologic studies", Neurology, 1996, 47(2), 425-432.

McGeer et al. "Glial cell reactions in neurodegenerative diseases: pathophysiology and therapeutic interventions", Alz Dis Accos Dis, 1998, 12(Sul 2), S1-S6.

McGeer et al. "Inflammation of the brain in Alzheimer's disease: implications for therapy", J Leukoc Biol, 1999, 65, 409-415.

McGeer et al. "Reactive microglia in patients with senile dementia of the Alzheimer type are positive for the histocompatibility glycoprotein HLA-DR", Neurosci Lett, 1987, 79, 195-200.

McKhann et al. "Clinical diagnosis of Alzheimer's disease", Neurology, 1984, 34, 939-944.

McKintosh et al. "Prion diseases", J of Neuro Virology, 2003, 9, 183-193.

McMillian et al. "Dopamine Stimulates [sup3H]Phorbol 12, 13-Dibutyrate Binding in Cultured Striatal Cells", J Neurochem, 1992, 58(4), 1308-1312.

McMillian et al. "Selective killing of cholinergic neurons by microglial activation in basal forebrain mized neuronal/glial cultures", Biochem Biophys Res Commun, 1995, 215(2), 572-577.

Meda et al. "Activation of microglial cells by beta-amyloid protein and interferon-gamma", Nature, 1995, 374, 647-650.

Mehta et al. "Plasma and cerebrospinal fluid levels of amyloid [beta] proteins 1-40 and 1-42 in Alzheimer disease", Arch Neurol, 2000, 57(1), 100-105.

Meyer et al.. "APOE genotype predicts when—not whether—one is predisposed to develop Alzheimer disease", Nat Genet al. 1998, 19, 321-322.

Milstien et al. "Cerebrospinal fluid nitrite/nitrate levels in neurologic diseases", J Neurochemistry, 1994, 63, 1178-1180.

Miyata et al. "Apolipoprotein E allele-specific antioxidant activity and effects on cytotoxicity by insults and beta-amyloid peptides", Nat Genet al. 1996, 14, 55-61.

Mok et al. "Clinicopathological concordance of dementia diagnoses by community versus tertiary care clinicians", Am J Alzheimers Dis Other Demen Author manuscript, 2006, 1-8.

Morgello et al. "The National NeuroAIDS tissue consortium: a new paradigm in brain banking with an emphasis on infectious disease", Neuropath A Neurobiol, 2001, 27, 326-335.

Morris "The clinical dementia rating (CDR): current version and scoring rules", Neurology, 1993, 43, 2412-2414.

Mourdian et al. "No changes in central quinolinic acid levels in Alzheimer's disease", Neurosci Lett, 1989, 105, 233-238.

Mrak et al. "Glial cytokines in Alzheimer's disease: review and pathogenic implications", Hum Pathol, 1995, 26(8), 816-823.

Namba et al. "Apolipoprotein E immunoreactivity in cerebral amyloid deposits and neurofibrillary tangles in Alzheimer's disease and kuru plaque amyloid in Creutzfeldt-Jakob disease", Brain Res, 1991, 541, 163-166.

Nathan et al. "The inhibitory effect of apolipoprotein E4 on neurite outgrowth is associated with microtubule depolymerization", J Biol Chem, 1995, 270(34), 19791-19799.

Netland et al. "Indomethacin reverses the microglial response to amyloid beta-protein", Neurobiol Aging, 1998, 19(3), 201-204.

Ohe et al. "Effect of p-glycoprotein-mediated efflux on cerebrospinal fluid/plasma concentration ratio", Drug Metabolism Disposition, 2003, 31, 1251-1254.

Overmyer et al. "Reactive microglia in aging and dementia: an immunohistochemical study of postmortem human brain tissue", Acta Neuropath, 1999, 97, 383-392.

Pasinetti et al. "Cyclooxygenase and inflammation in Alzheimer's disease: experimental aroaches and clinical interventions", J Neurosci Res, 1998, 54, 1-6.

Perlmutter et al. "MHC class II-positive microglia in human brain: Association with Alzheimer lesions", J Neurosci Res, 1992, 33, 549-558.

Perry et al. "The influence of systemic inflammation on inflammation in the brain: implications for chronic neurodegenerative disease", Brain, Behavior, and Immunity, 2004, 18, 407-413.

Petersen et al. "Apolipoprotein E status as a predictor of the development of Alzheimer's disease in memory-impaired individuals", JAMA, 1995, 273(16), 1274-1278.

Peterson et al. "Thalidomide inhibits tumor necrosis factor-alpha production by lipopolysaccharide and lipoarabinomannan-stimulated human microglial cells", J Infect Dis, 1995, 172, 1137-1140.

Pham et al. "Cerebral uptake of mefloquine enatiomers in fatal cerebral malaria", J Clin Pharmacol Ther, 1999, 37(1), 58-61.

Piani et al. "Murine brain macrophages induce NMDA receptor mediated neurotoxicity in vitro by secreting glutamate", Neurosci Lett, 1991, 133, 159-162.

Piedrahita et al. "Generation of mice carrying a mutant apolipoprotein E gene inactivated by gene targeting in embryonic stem cells", Proc Natl Acad Sci USA, 1992, 89, 4471-4475.

Pikas et al. "Substrate specificity of heparanases from human hepatoma and platelets", J Biol Chem, 1998, 273(30), 18770-18777.

Pike et al. "Neurodegeneration induced by beta-amyloid peptides in vitro: the role of peptide assembly state", J Neuroscience, 1993, 13(4), 1676-1687.

Podlisny et al. "Synthetic amyloid beta-protein fails to produce specific neurotoxicity in monkey cerebral cortex", Neurobiol Aging, 1992, 13, 561-567.

Poirier et al. "Apolipoprotein E4 allele as a predicator of cholinergic deficits and treatment outcome in Alzheimer's disease", Proc Natl Acad Sci, 1995, 92, 12260-12264.

Powderly "Sorting through confusing messages: the art of HAART", JAIDS, 2002, 31(Sul 1), S3-S9.

Price "The two faces of HIV infection of cerebrospinal fluid", Trends Microbiol, 2000, 8(9), 387-390.

Price et al. "Neurological outcomes in late HIV infection: adverse impact of neurological impairment on survival and protective effect of antiviral therapy", AIDS, 1999, 13(13), 1677-1685.

Price et al. "Neuron number in the entorhinal cortex and CA1 in preclinical Alzheimer disease", Arch Neurol, 2001, 58(9), 1395-1402.

Price et al. "Toxicity of synthetic Abeta peptides and modeling of Alzheimer's disease", Neurobiol Aging, 1992, 13, 623-625.

Pulliam et al. "Human immunodeficiency virus-infected macrophages produce soluble factors that cause histological and neurochemical alternations in cultured human brains", J Clin Invest, 1991, 87, 503-512.

Pye et al. "Heparan sulfate oligosaccharides require 6-O-sulfation for promotion of basic fibroblast growth factor mitogenic activity", J Biol Chem, 1998, 273(36), 22936-22942.

Queiroz et al. "A rapid, specific, and sensitive method for the determination of acetylation phenotype using dapsone", J Anal Toxicol, 1997, 21, 203-207.

Rasmusson et al. "Predicting rate of cognitive decline in probable Alzheimer's disease", Brain & Cognition, 1996, 31, 133-147.

Rasquin et al. "Predictive accuracy of MCI subtypes for alzheimer's disease and vascular dementia in subjects with mild cognitive impairment: a 2-year follow-up study", Dement Geriatr Cogn Disord, 2005, 19(2-3), 113-119, abstract, 1 page, http://wwwncbinImnihgov/sites/entrez?Db=pubmed&Cmd=SnowDetailView&Ter—m, downloaded from the internet on Aug. 15, 2007.

Rezaie "Microglia and the pathogenesis of spongiform encephalopathies", Brain Reviews, 2001, 35, 55-72.

Rio-Hortega "Microglia", Cytology and Cellular Pathology of the Nervous System, Hocker, Inc, NY, Penfield, W (Ed), 1932, 481-533.

Rodriguez et al. "Dapsone prevents morphological lesions and lipid peroxidation induced by quinolinic acid in rat corpus striatum", Toxicology, 1999, 139(50), 111-118.

Rogers et al. "Clinical trial of indomethacin in Alzheimer's disease", Neurology, 1993, 43, 1609-1611.

Rogers et al. "Complement activation and beta-amyloid-mediated neurotoxicity in Alzheimer's disease", Res Immunol, 1994, 146, 624-630.

Rogers et al. "Expression of immune system-associated antigens by cells of the human central nervous system: relationship to the pathology of Alzheimer's disease", Neurobiol Aging, 1988, 9, 339-349.

Roher et al. "Isolation and characterization of Alzheimer's disease paired helical filament cytoskeletons: differentiation from amyloid plaque core protein", J Cell Biol, 1988, 107(No. 6, Pt 2), 2703-2716.

Roher et al. "Structural alterations in the peptide backbone of beta-amyloid core protein may account for its deposition and stability in Alzheimer's disease", J Biol Chem, 1993, 268(5), 3072-3083.

Rossler et al. "Stage-dependent and sector-specific neuronal loss in hiocampus during Alzheimer's disease", Acta Neuropathol, 2002, 103, 363-369.

Rubin et al. "Very mild senile dementia of the Alzheimer's type, I Clinical assessment", Arch Neurol, 1989, 46, 379-382.

Russo et al. "Opposite roles of apolipoprotein E in normal brains and in Alzheimer's disease", Proc Natl Acad Sci USA, 1998, 95, 15598-15602.

Sacktor et al. CSF antiretroviral drug penetrance and the treatment of HIV-associated psychomotor slowing, Neurology, 2001, 57, 542-544.

Salmivirta et al. "Differentiation associated modulation of heparin sulfate structure and function in CaCo-2 colon carcinoma cells", Glycobiology, 1998, 8(10), 1029-1036.

Saunders et al. "Association of apolipoprotein E allele epsilon4 with late-onset familial and sporadic Alzheimer's disease", Neurology, 1993, 43, 1467-1472.

Saunders et al. "The role of apolipoprotein E in Alzheimer's disease: pharmacogenomic target selection", Biochim Biophys Acta, 2000, 1502, 85-94.

Savion et al. "Murine macrophage heparanase: inhibition and comparison with metastatic tumor cells", J Cell Physiol, 1987, 130, 77-84.

Schifitto et al. "Clinical trials in HIV-associated cognitive impairment: cognitive and functional outcomes", Neurology, 2001, 56, 415-418.

Schmechel et al. "Increased amyloid beta-peptide deposition in cerebral cortex as a consequence of apolipoprotein E genotype in late-onset Alzheimer disease", Proc Natl Acad Sci USA, 1993, 90, 9649-9653.

Schwarcz et al. "Quinolinic acid: an endogenous metabolite that produces axon-sparing lesions in rat brain", Science, 1983, 219, 316-318.

Selkoe "Physiological production of the beta-amyloid protein and the mechanism of Alzheimer's disease", Trends Neurosci, 1993, 16(10), 403-409.

Selkoe "The molecular pathology of Alzheimer's disease", Neuron, 1991, 6, 487-498.

Senior "Dosing in phase II trial of Alzheimer's vaccine suspended", Lancet Neurol, 2002, 1, 3.

Sghirlanzoni et al. "Chloroquine myopathy and myasthenia-like syndrome", Muscle Nerve, 1988, 11, 114-119.

Sharma et al. "Pharmacological basis of drug therapy of Alzheimer's disease", Indian Journal of Experimental Biology, 35, Nov. 1, 1997, 1146-1155.

Shearman et al. "The intracellular component of cellular 3-(4,5-dimethylthiazol-2-yl)-2,5-diphenyltetrazolium bromide (MTT) reduction is specifically inhibited by beta-amyloid peptides", J Neurochem, 1995, 65(1), 218-227.

Shimada et al. "Subendothelial extracellular—matrix heparan sulfate proteoglycan-degrading activity of human monocyte macrophages", Heart Vessels, 1987, 3, 175-181.

Singh et al. "Toxicity profiles of disease modifying antirheumatic drugs in rheumatoid arthritis", J Rheumatol, 1991, 18(2), 188-194.

Singhal et al. "Antitumor activity of thalidomide in refractory multiple myeloma", N Engl J Med, 1999, 341(21), 1565-1571.

Spillmann et al. "Defining the interleukin-8-binding domain of heparan sulfate", J Biol Chem, 1998, 273(25), 15487-15493.

Strategic Management of Antiretroviral Therapy (SMART), Study Protocol, 2001 Version 10, 2-4.

Strittmatter et al. "Binding of human apolipoprotein E to synthetic amyloid beta peptide: isoform-specific effects and implications for late-onset Alzheimer disease", Proc Natl Acad Sci USA, 1993, 90, 8098-8102.

Strittmatter et al. "Isoform-specific interactions of apolipoprotein E with microtubule-associated protein tau: Implications for Alzheimer disease", Proc Natl Acad USA, 1994, 91, 11183-11186.

Surrey et al. "The Preparation of 7-Chloro-4-(4-(N-ethyl-N-beta-hydroxyethylamino)-1-methylbutylamino)-quinoline and Related Compounds", J Am Chem Soc, 1950, 72, 1814-1815.

Taylor "Anticholinesterase Agents", Goodman and Gilman's The Pharmacological Basis of Therapeutics, 8supth Ed, 1992, 131, 147-149.

Terry "Alzheimer's disease: clinical aspects, function, and frequency", Textbook of Neuropathology, Robertson, CM, Ed, Williams and Wilkins, Baltimore, 1985, 824-841.

Terry et al. "Structural basis of the cognitive alterations in Alzheimer disease", Alzheimer Disease, Raven Press, NY, Terry, RD, et al (Eds), 1994, 179-196.

Terry et al. "The neuropathology of Alzheimer disease and the structural basis of its cognitive alterations", Alzheimer Disease 2supnd Ed, Raven Press, NY, Terry, RD, et al (Eds), 1999, 187-206.

Teter et al. "Human apolipoprotein E isoform-specific differences in neuronal sprouting in organotypic hiocampal cultures", J Neurochem, 1999, 73(6), 2613-2616.

The NIA-Reagan Working Group, "Consensus recommendations for the postmortem diagnosis of Alzheimer's disease", Neurobiol Aging, 1997, 18(S4), S1-S2.

Thery et al. "Cytotoxic Effect of Brain Macrophages on Developing Neurons", Eur J Neurosci, 1991, 3, 1115-1164.

Thery et al. "Neurotoxicity of brain macrophages", Clin Neuropathol, 1993, 12, 288-290.

Tierney et al. "A prospective study of the clinical utility of ApoE genotype in the prediction of outcome in patients with memory impairment", Neurology, 1996, 46, 149-154.

Tingle et al. "Comparison of metabolism and toxicity of dapsone in rat, mouse, and man", J Pharm Exp Therap, 1997, 283, 817-823.

Toukko et al. "Cognitive impairment: concepts and issue", Int Psychogeriatr, 2001, Su 1, 183-202.

Trevitt et al. "A systematic review of prion therapeutics in experimental models", Brain, 2006, 129, 2241-2265.
Van den Berg et al. "Serial cerebrospinal fluid sampling in a rat model to study drug uptake from the nasal cavity", J Neurosci Meth, 2002, 116, 99-107.
Van Gool et al., "Effect of hydroxychloroquine on progression of dementia in early Alzheimer's disease: an 18-month randomised, double-blind, placebo-controlled study", Lancet al. 358(9280), Aug. 11, 2001, 455-460.
Vezmar et al. "Direct binding of chloroquine to the multidrug resistance protein (MRP): possible role for MRP in chloroquine drug transport and resistance in tumor cells", Biochem Pharmacol, 1998, 56, 733-742.
Visser et al. Do MCI criteria in drug trials accurately identify subjects with predementia alzheimer's disease?, J Neurol Neurosurg Psychiatry, 2005, 76, 1348-1354.
Vitkovic et al. "Neuropathogenesis of HIV-1 infection Outstanding questions", Medical Sciences, 1998, 321, 1015-1021.
Von Giesen et al. "Therapeutic effects of nonnucleoside reverse transcriptase inhibitors on central nervous system in HIV-1 infected patients", JAIDS, 2002, 29, 363-367.
Wadsworth et al. "Molecular and clinical classification of human prion disease", British Medical Bulletin, 2003, 66, 241-254.
Watkins "Brain not inflamed?" Sci American, Nov. 24-26, 2003.
Wenham et al. "Apolipoprotein E genotyping by one-stage PCR", Lancet al. 1991, 337, 1158-1159.
West et al. "The CA1 region of the human hiocampus a hot spot in Alzheimer's disease", Ann NY Acad, 2000, 908, 255-259.
West et al. "Unbiased stereological estimation of the total number of neurons in the subdivisions of the rat hiocampus using the optical fractionator", Anat Rec, 1991, 231, 482-497.
Whitson "Attenuation of the neurotoxic effect of Abeta amyloid peptide by apolipoprotein E", Biochem Biophys Res Commun, 1994, 199(1), 163-170.
Wilcock et al. "Plaques, tangles and dementia", J Neurol Sci, 1982, 56, 343-356.

Williams-Ashman et al. "Trends in the biochemical pharmacology of 5'deoxy5'methylthioadenosine", Biochem Pharmacol, 1982, 31(3), 277-299.
Wisniewski et al. "Ultrastructure of cells forming amyloid fibers in Alzheimer disease and scrapie", Am J Med Human Genet al. 1990, 7, 287-297.
Wojtera et al. "Microglial cells in neurodegenerative disorders", Folia Neuropath, 2005, 43(4), 311-321.
Wolfson et al. "A case-control analysis of nonsteroidal anti-inflammatory drugs and Alzheimer's disease are they protective?", Neuroepidmiol, 2001, 358, 81-86.
Working Group of American Academy of Neurology AIDS Task Force, "Nomenclature and research case definitions for neurologic manifestations of human immunodeficiency virus-type 1 (HIV-1) infection", Neurology, 1991, 41, 778-785.
Wujek et al. "Deposits of Abetafibrils are not toxic to cortical and hiocampal neurons in vitro", Neurobiol Aging, 1996, 17(1), 107-113.
Yahalom et al. "Differentiating human leukemia cells express heparanase that degrades heparan sulfate in the subendothelial extracellular matrix", Leuk Res, 1988, 12(9), 711-717.
Yankner et al "beta-amyloid and the pathogenesis of Alzheimer's disease", New Eng J Med, 1991, 325(26), 1849-1857.
Yankner et al. "Neurotrophic and neurotoxic effects of amyloid beta protein: reversal by tachykinin neuropeptides", Science, 1990, 250, 279-282.
Yeni et al. "Antiretroviral treatment for adult HIV infection in 2002: updated recommendations of the international AIDS society-USA panel", JAMA, 2002, 288(2), 222-235.
Younkin "Evidence that Abeta42 is the real culprit in Alzheimer's disease", Ann Neurol, 1995, 37, 287-288 55 FR 9576, 1990, Part 4931253, http:/wwwphocdcgov/clia/regs/tocaspx.
Zhan et al. "Distribution of beta amyloid associated proteins in plaques in Alzheimer's disease and in the non-demented elderly", Neurodegeneration, 1995, 4, 291-297.

* cited by examiner

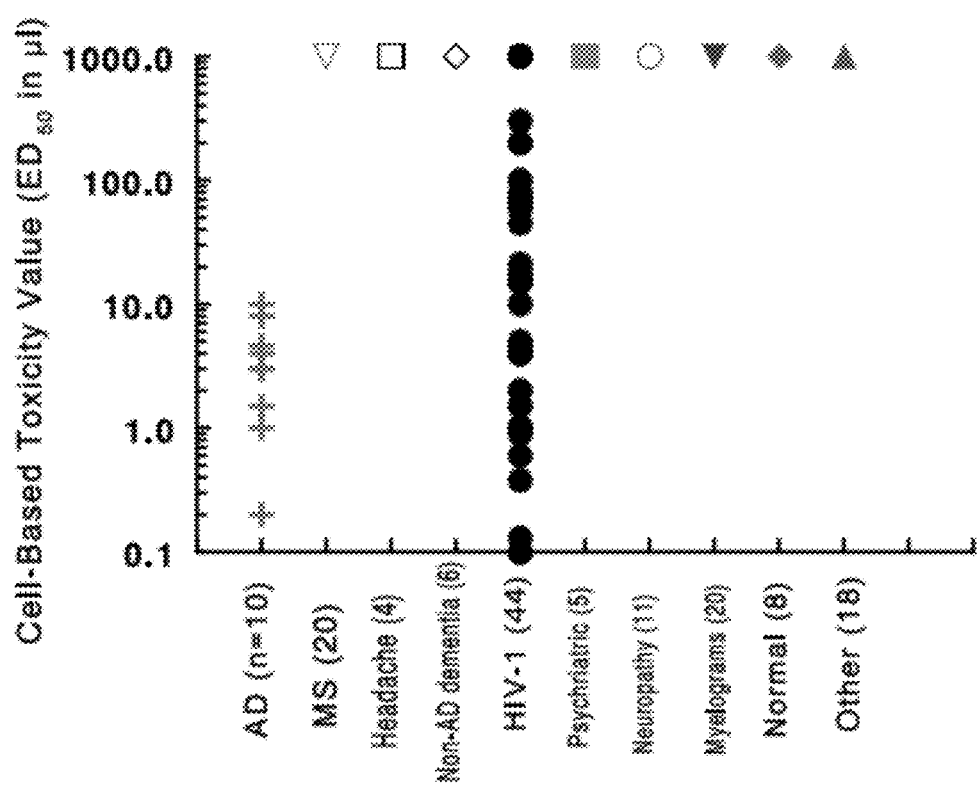

Figure 8C
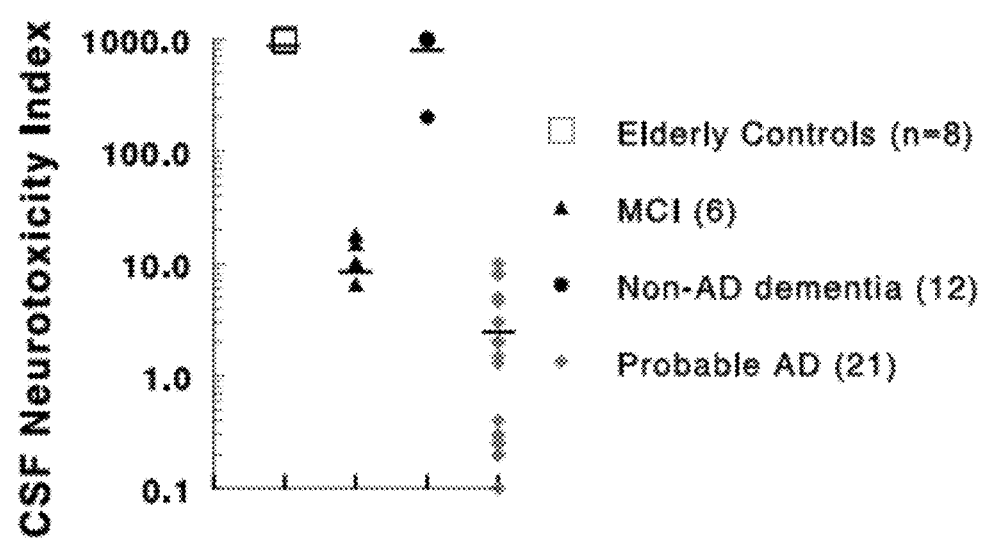

METHODS FOR DIAGNOSIS AND MONITORING OF NEUROLOGICAL DISEASE BY DETECTION OF AN EXCEPHALOTOXIN

CROSS-REFERENCE TO RELATED APPLICATIONS

This application is a continuation of U.S. application Ser. No. 11/970,587, filed Jan. 8, 2008, which is a continuation of U.S. application Ser. No. 10/543,486, now U.S. Pat. No. 7,344,853, which is the national stage of International Application No. PCT/US2004/02236, filed Jan. 27, 2004, which claims the benefit of U.S. Provisional Application No. 60/443,219, filed Jan. 27, 2003. The contents of each of the applications are incorporated by reference herein in their entirety.

REFERENCE TO GOVERNMENT GRANTS

This invention was made with government support under Grant No. AG12548 awarded by the National Institutes of Health. The government may have certain rights in the invention.

FIELD OF THE INVENTION

The invention relates to the correlation of clinical manifestations of neurological disease with a neurotoxin produced by affected brain mononuclear phagocytes. The invention also relates to methods for diagnosing a neurological disease or risk for loss of cognition by detecting a neurotoxin in a biological sample of a subject. The neurotoxin, encephalotoxin, has been found to be released by an inflammatory cascade that chronically damages neurons in neurological disease, for example, HIV-1-associated dementia (HAD), neuro-AIDS, Creutzfeldt-Jakob Disease, Mild Cognitive Impairment, prion disease, minor cognitive/ motor dysfunction, acute stroke, acute trauma, and Alzheimer's disease (AD). The inflammatory cascade involves activation of mononuclear phagocytes and loss of synaptic connections and neurons, thus resulting in a decline in information processing, attention, learning, and information retrieval with overall loss of intellectual function.

BACKGROUND OF THE INVENTION

Loss of cognition and dementia associated with neurological disease results from damage to neurons and synapses that serve as the anatomical substrata for memory, learning, and information processing. Despite much interest, biochemical pathways responsible for progressive neuronal loss in these disorders have not been elucidated.

Alzheimer's disease (AD) accounts for more than 15 million cases worldwide and is the most frequent cause of dementia in the elderly (Terry, R. D. et al. (eds.), ALZHEIMER'S DISEASE, Raven Press, New York, 1994). AD is thought to involve mechanisms which destroy neurons and synaptic connections. The neuropathology of this disorder includes formation of senile plaques which contain aggregates of Aβ1-42 (Selkoe, *Neuron,* 1991, 6:487-498; Yankner et al., *New Eng. J. Med.,* 1991, 325:1849-1857; Price et al., *Neurobiol. Aging,* 1992, 13, 623-625; Younkin, *Ann. Neurol.,* 1995, 37:287-288). Senile plaques found within the gray matter of AD patients are in contact with reactive microglia and are associated with neuron damage (Terry et al., "Structural Basis of the Cognitive Alterations in Alzheimer Disease", ALZHEIMER'S DISEASE, NY, Raven Press, 1994, Ch. 11, 179-196; Terry, R. D. et al. (eds.), ALZHEIMER'S DISEASE, Raven Press, New York, 1994; Perlmutter et al., *J. Neurosci. Res.,* 1992, 33:549-558). Plaque components from microglial interactions with Aβ plaques tested in vitro were found to stimulate microglia to release a potent neurotoxin, thus linking reactive microgliosis with AD neuronal pathology (Giulian et al., *Neurochem. Int.,* 1995, 27:119-137).

Several lines of evidence now support the concept that microglia-derived neurotoxins contribute to AD pathology. First, microglia-derived toxins can be extracted from AD brain regions laden with plaques but not from identical brain regions in age-matched control or ALS brain tissues (Giulian et al. (1995) *Neurochem. Int.,* 27: 119-137; Giulian et al. (1996) *J. Neurosci.,* 16: 6021-6037). Second, regional distributions of toxic activity show the greatest concentrations of microglia-derived neuron poisons in neocortical tissues and hippocampi of AD (vs. controls or ALS), areas containing large numbers of reactive microglia. In contrast, cerebellum, white matter, and neocortical tissues from normal or ALS patients, which had few, if any, reactive microglial clusters, show little neurotoxic activity. Moreover, the relative number of reactive microglial clusters in each brain region is significantly correlated to the level of neurotoxic activity extracted from that region ($p<0.005$). Third, isolated plaque fragments or synthetic human Aβ1-40 or Aβ1-42 peptides are found to activate human microglia to release neurotoxins in culture (Giulian et al. (1995) *Neurochem. Int.,* 27: 119-137; Giulian et al. (1996) *J. Neurosci.,* 16: 6021-6037). No neurotoxic effects, however, are detected when plaques or peptides were placed directly atop neurons or when microglia are exposed to fractions lacking plaques isolated from AD, ALS, or normal, aged control brains (Giulian et al. (1995) *Neurochem. Int.* 27: 119-137; Giulian et al. (1996) *J. Neurosci.* 16: 6021-6037). Thus, the toxic effects of isolated plaques on neurons are indirect and mediated by a neurotoxic activity released from plaque-stimulated microglia. Fourth, there is neurotoxic activity found in CSF from AD patients, but not detected in samples from disease controls (U.S. Pat. No. 6,043,283 to Giulian; Giulian et al. (1999) *Am. J. Hum. Genet.,* 65:13-18). Fifth, infusion of Aβ-coupled microspheres into hippocampus produces inflammatory responses at the site of infusion in rats (U.S. Pat. No. 6,043,283 to Giulian). Together, these data indicate that plaque-activation of microglia through contact with Aβ peptides produces neuron-killing factors in discrete areas of AD brain (Giulian et al. (1995) *Neurochem. Int.,* 27: 119-137).

Although most patients developing AD will go through a transient period of mild cognitive impairment (MCI), they will often not present to a physician during this early phase of the disease. There is a consensus among research groups that subjects with MCI are at increased risk for progressing to AD (Grundman et al. (1996) *Neurology* 46:403; Flicker et al. (1991) *Neurology* 41:1006-1009; Masur et al. (1994) *Neurology* 44:1427-1432; Tierney et al. (1996) *Neurology* 46:149-154). Memory impairment is commonly the most prominent feature of MCI but might include other patterns including defects primarily in language or visuomotor performance (Hughes et al. (1982) *Br. J. Psychiatry,* 140:566-572; Berg (1988) *Psychopharmacol. Bull.,* 24:637-639; Morris (1993) *Neurology,* 43:2412-2414; Rubin et al. (1989) *Arch. Neurol.,* 46:379-382; Grundman et al. (1996) *Neurology,* 46:403; Flicker et al. (1991) *Neurology,* 41:1006-1009; Masur et al. (1994) *Neurology,* 44:1427-1432;Tierney et al. (1996) *Neurology,* 46:149-154). Attempts at characterizing mild cognitive impairment have been carried out using the Clinical Dementia Rating (CDR) Scale, which rates the severity of dementia as absent, mild, moderate, or severe. Rubin et al. ((1989) *Arch. Neurol.,* 46:379-382) concluded that individuals with a CDR of 0.5 likely have "very mild" AD in the majority of cases [The CDR 0.5 classification is characterized by consistent forgetfulness, which is mild with little if any impairment in other functions such as orientation, community affairs, home, and hobbies, judgment, and personal care.] Other measures also have been used to identify MCI subjects. For example, poor delayed recall has been shown to be the best predictor of progression, the best predictor of subsequent dementia in non demented elderly subjects, and the best discriminator between normal aging and mild AD (Flicker et al. (1991) *Neurology,* 41:1006-1009; Masur et al. (1994) *Neurology,* 44:1427-1432; Tierney et al. (1996) *Neurology,* 46:149-154). The time required for subjects with MCI to develop a clinical diagnosis of AD has been estimated by the Alzheimer's Disease Cooperative Study (ADCS) at about 30% at 2 years and 45% at 3 years.

HIV-1 infection and neuro-AIDS produce devastating effects upon the brain and spinal cord. Although the underlying anatomical basis for impaired cognition during HIV-1 infection remains obscure, there is a reduction of up to 40% of large neurons scattered throughout the neocortex in advanced disease with dementia (Masliah et al. (1992) *J. Neuropath Exp Neurol.,* 51: 585-593) and a striking early loss of synapses (Asare et al. (1996) *Am J Path* 148: 31-38; Everall et al. (1993) *J. Neuropath. Exp. Neurol.* 52: 561-566).

HIV-1 associated dementia (HAD) is characterized by cognitive dysfunction, declining motor performance, and behavioral changes. It occurs primarily in the more advanced stages of HIV infection when CD4 cell counts are relatively low. While the progression of dysfunction is variable, it is regarded as a serious complication with fatal outcome. The diagnosis of cognitive loss due to HIV is by process of exclusion—no approved marker exists to monitor HIV-specific injury to the CNS. Without such a marker, there are no clinical indications to evaluate patients until significant functional loss appears and there are few opportunities to develop new treatment strategies to prevent HIV brain damage. Therefore, it is very desirable to identify patients at early pre-symptomatic stages.

Prior to HAART (defined here as combination therapy using 3 or more anti-retroviral agents), 60% of those with AIDS developed dementia. This incidence appears to have fallen to about 10 to 15%, but cognitive dysfunction remains a problem for over half of the HIV/AIDS population (Giulian et al. (1990) *Science,* 250: 1593-1596; Giulian et al. (1993) *Proc. Natl. Acad. Sci.,* 90:2769-2773; Giulian (1995) In: NEUROGLIA (II Kettenmann, B Ransom Eds) Oxford University Press, pp. 671-684; Giulian et al. (1998) In: INFLAMMATORY MECHANISMS OF NEURODEGENERATION AND ITS MANAGEMENT (P. Wood, ed.); Humana Press, Vol 4, pp. 109-128).

HIV-1 brain pathology involves diffuse synaptic damage in the neocortex, the loss of cortical neurons, and a population of infected, reactive mononuclear phagocytes, including invading blood monocytes, microglia, and multi-nucleated giant cells. These giant cells represent a fusion of HIV-infected mononuclear phagocytes that are coated with gp120, the retroviral envelope protein; presence of giant cells has been correlated with cognitive impairment during HIV-1 infection. Currently, most research groups in the field agree that poisons released by infected mononuclear phagocytes are a primary cause of cognitive loss in the HIV-1(+) population (Vitokovic et al. (1998) *Medical Sciences,* 321: 1015-1021; Morgello et al. (2001) *Neuropath. App. Neurobiol.,* 27: 326-335; Lawrence et al. (2002) *Microbes and Infection,* 4: 301-308; Masliah et al. (1992) *J. Neuropath. Exp. Neurol.,* 51: 585-593; Maslliah et al. (1995) *J. Neuropath. and Exp. Neurol.,* 54: 350-357; Asare et al. (1996) *Am. J. Path.,* 148: 31-38; Everall et al. (1993) *J. Neuropath. Exp. Neurol.,* 52: 561-566).

Several lines of evidence now support the concept that mononuclear phagocyte-derived neurotoxins contribute to the neuron injury within brain during HIV-1 infection. First, HIV-1 neither infected neurons nor showed a direct toxic effect upon neurons (Giulian et al. (1996) *J. Neurosci.,* 16:3139-3153, Giulian et al. (1990) *Science* 250: 1593-1596; Levine et al. (1976) *Biochim. Biophys. Acta,* 452: 458-467). Second, HIV-1 mononuclear phagocytes (THP-1, U937, human blood monocytes, and human brain microglia) released neurotoxins when infected in vitro with HIV-1; in contrast, lymphocytes (H9, human blood lymphocytes) did not (Giulian et al. (1996) *J. Neurosci.,* 16:3139-3153; Giulian et al. (1990) *Science,* 250: 1593-1596). Third, human mononuclear phagocytes (blood monocytes and microglia) isolated from infected donors released the same neurotoxin as recovered from in vitro experiments; again, isolated infected lymphocytes did not (Giulian et al. (1996) *J. Neurosci.,* 16:3139-3153). Fourth, neurotoxic activity can be recovered from brain tissues of infected individuals (Giulian et al. (1993) *Proc. Natl. Acad. Sci.,* 90:2769-2773; Giulian (1995) In: NEUROGLIA (H Kettenmann, B Ransom, Eds,) Oxford University Press, pp. 671-684; Giulian et al. (1998) In: INFLAMMATORY MECHANISMS OF NEURODEGENERATION AND ITS MANAGEMENT (P. Wood, ed.); Humana Press, Vol 4, pp. 109-128). Fifth, gp120, the viral envelope glycoprotein, can stimulate neurotoxin release from human blood monocytes and microglia; other viral proteins including that did not (Levine et al. (1976) *Biochim. Biophys. Acta,* 452: 458-467). Sixth, high concentrations of neurotoxin were found in the cerebrospinal fluid of HIV-1(+) individuals. And seventh, a family of neurotoxic heparan oligosaccharides can be isolated from HIV-1 infected cells and from HIV CSF.

Although reactive mononuclear phagocytes release a number of bio-active substances, few of these compounds are actually able to harm neurons at concentrations found to exist in neurodegenerative disease (Hardy et al. (2002) *Science,* 297:353; Mourdian et al., (1989) *Neurosci. Lett.,* 105: 233; Milstein et al. (1994) *J. Neurochemistry,* 63, 1178; Giulian et al. (1990) *Science,* 250:1593). Moreover, few of such candidate neuron poisons are present in both AD and HAD. For example, increased tissue concentrations of "toxic" forms of Aβ1-42 are characteristic for AD (Hardy et al. (2002) *Science,* 297:353), but do not occur in HAD. Similarly, elevated quinolinic acid levels occur in the cerebrospinal fluid (CSF) of subjects with HAD (Mourdian et al. (1989) *Neurosci. Lett.,* 105:233), but not in those with AD (Milstein, et al. (1994) *J. Neurochemistry,* 63: 1178). In contrast, both AD and HAD brain tissues contain a heterogeneous group of small stable molecules with potent neurotoxic actions (Giulian et al. (1990) *Science,* 250:1593; Giulian et al. (1995) *Neurochem. Int.,* 27:119; Giulian et al. (1996) *J. Neuroscience* 16: 6021). Cultured mononuclear phagocytes activated by exposure to amyloid plaques, synthetic β-amyloid peptides, HIV-1, or gp120, produce these same neurotoxins (Giulian, et al. (1993) *Proc. Natl. Acad. Sci. USA,* 90: 2769; Giulian et al. (1998) *J. Biol. Chem.,* 273: 29719). Such observations suggest that a common, though unidentified, pathway mediates immune-driven neuron pathology in both AD and HAD.

As the clinical expression of neurological disease may occur only after a significant degree of neuron loss and synaptic damage beyond a critical threshold necessary for adequate adaptive function, early pre-symptomatic detection of disease pathology offers the opportunity to slow disease progression. The present invention provides methods for diagnosis of neurological disease and risk for loss of cognition, including, for example, Alzheimer's disease, HIV-1 associated dementia (HAD), neuro-AIDS, Creutzfeldt-Jakob disease, Mild Cognitive Impairment (MCI), prion disease, minor cognitive/ motor dysfunction, acute stroke, or acute trauma. The methods of the invention allow early detection of neurological disease and risk for loss of cognition, thereby allowing earlier intervention in the progression of disease. Also provided are methods for monitoring the progression and treatment of neurological disease by monitoring encephalotoxin levels in a subject.

SUMMARY OF THE INVENTION

The present invention provides various embodiments of methods for diagnosis of neurological disease or risk for loss of cognition in a subject. This is accomplished by detecting an encephalotoxin in a biological sample of the subject. In some embodiments of the invention, detection of the encephalotoxin involves contacting a biological sample of the subject with neurons both in the presence of and in the absence of an inactivator of the encephalotoxin and comparing neuron survival in the presence of the encephalotoxin inactivator relative to neuron survival in the absence of the encephalotoxin inactivator. A decrease in neuron survival in the absence of the encephalotoxin inactivator is indicative of the neurological disease or risk for loss of cognition. In some embodiments of the invention, encephalotoxin is detected by measuring light absorbance of the biological sample in the both the presence of and in the absence of a encephalotoxin inactivator, an increase in absorbance in the absence of the encephalotoxin inactivator being indicative of neurological disease or risk for loss of cognition. Preferably, light absorbance is measured at a wavelength of 232 nanometers (nm).

In some embodiments of the invention, the encephalotoxin is an oligosaccharide having at least one glucosamine having N-sulfation and O6-sulfation; lacking peptide bonds; and having a molecular mass of less than about 2000 daltons. Preferably, the encephalotoxin has 4 to 8 saccharide units. Preferably, the molecular mass of the encephalotoxin is between about 700 and 1900 daltons.

In some embodiments, the encephalotoxin inactivator is heparin lyase I, nitrous acid, glucosamine-6-sulfatase, or N-sulfamidase. Preferably, the nitrous acid solution has a pH of about 1.5.

In some embodiments of the invention, the biological sample is cerebrospinal fluid, spinal cord tissue, or brain tissue.

Neurological diseases that may be diagnosed or monitored by the methods of the invention include neurodegenerative and neuro-inflammatory diseases and disorders such as, but not limited to, Alzheimer's Disease, Creutzfeldt-Jakob Disease, Human Immunodeficiency Virus-1 (HIV-1)-associated dementia (HAD), Mild Cognitive Impairment (MCI), prion disease, minor cognitive/ motor dysfunction, acute stroke, acute trauma, and neuro-AIDS. In various embodiments, the methods of the invention may be used in the diagnosis or monitoring of human, primate, bovine, equine, canine, feline, porcine, or rodent subjects.

In some embodiments of the invention, comparison of neuron survival comprises comparison of the $ED_{50}$ of the encephalotoxin in the presence of the encephalotoxin inactivator relative to the $ED_{50}$ of the encephalotoxin in the absence of the encephalotoxin inactivator, wherein a lower $ED_{50}$ of the encephalotoxin in the absence of encephalotoxin inactivator relative to the $ED_{50}$ of the encephalotoxin in the presence of encephalotoxin inactivator is indicative of neurological disease or risk for loss of cognition.

In further embodiments of the invention are provided methods of monitoring treatment of a neurological disease in a subject. In some embodiments, the method of monitoring involve comparing the encephalotoxin levels in a first and second biological sample of a subject, wherein the first biological sample is taken from the subject at an earlier timepoint than the second biological sample, wherein the second biological sample is taken from the subject following treatment of the neurological disorder, and wherein encephalotoxin level is measured by light absorbance of the biological sample, an increase in absorbance of the second biological sample being indicative of progression of the neurological disease. In some embodiments, the first biological sample is taken, removed, or extracted from the subject following a treatment (e.g., administration of a drug) of the neurological disease.

In further embodiments of the invention are provided methods of monitoring progression of neurological disease in a subject comprising detecting an increase in encephalotoxin level in said subject over time, wherein detecting the increase in encephalotoxin level comprises measuring an increased light absorbance of an encephalotoxin in a first biological sample of the subject relative to light absorbance of an encephalotoxin of a second biological sample of the subject, wherein the second biological sample is taken from the subject before the first biological sample, increased light absorbance being indicative of progression of the neurological disease.

Also provided by embodiments of the invention are methods for monitoring progression of neurological disease in a subject comprising detecting an increase in encephalotoxin level in the subject over time, wherein detecting the increase involves contacting a first biological sample of the subject with neurons, contacting a second biological sample of the subject with neurons, and detecting decreased neuron survival in the presence of the second biological sample, wherein the second biological sample is taken at a later timepoint than the first biological sample; and wherein decreased neuron survival in the presence of the second biological sample is indicative of progression of the neurological disease.

In some embodiments of the invention, one of the biological samples is taken during the prodromic phase of said neurological disease.

In another embodiment of the invention, methods of monitoring treatment of a neurological disease in a subject by detecting an increase in encephalotoxin level in a subject over time, wherein detecting the increase in encephalotoxin level involves contacting a first biological sample of the subject with neurons, contacting a second biological sample of the subject with neurons, and detecting decreased neuron survival in the presence of the second biological sample, wherein the second biological sample is taken at a later timepoint than the first biological sample and following a treatment of the neurological disease; and wherein decreased neuron survival is indicative of progression of the neurological disease.

BRIEF DESCRIPTION OF THE DRAWINGS

3.1.6.14) and N-sulfaminidase (E.C. 3.10.1.1)).

FIG. 8 illustrates the CSF Neurotoxicity Index, [calculated as value of equivalent volume of CSF to yield 50% of total killing effect upon a standardized rat hippocampal neuron culture assay] from cerebrospinal fluid (CSF) samples from a variety of neurological disorders. As shown in FIG. 8A, samples from definite Alzheimer's disease (AD) and HIV-1 infection contain encephalotoxins. Cerebrospinal fluid obtained during routine lumbar myelogram (Myelograms) were from subjects without memory complaints. Neuropathy refers to subjects with cranial or peripheral nerve disorders while subjects with psychiatric diagnoses had no evidence of neurological disease. Other neurological diseases included fungal meningitis, neuro-syphilis, multiple sclerosis (MS), and amyotrophic lateral sclerosis (ALS). FIG. 8C compares CSF index scores for elderly volunteers with no cognitive loss, with MCI, with probable AD, or with non-AD dementia (caused by traumatic, vascular, or ethanol injury). MCI shows a consistent and significantly elevated level of encephalotoxin above other forms of dementia. Bars show median values.

Figure 1A:
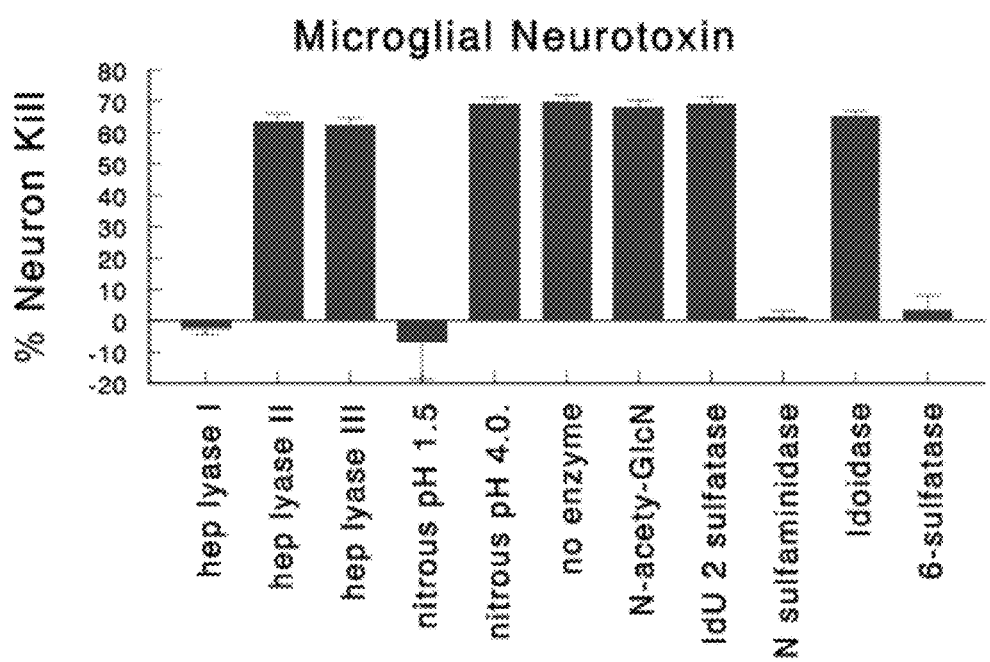
As shown in FIG. 1A, encephalotoxin released by BV2 microglia was inactivated by nitrous acid pH 1.5, by heparin lyase I (E.C. 4.2.2.7), and by sulfatases that cleave at O-6 and from N-sulfated glucosamine (GlcNS) (glucosamine-6-sulfatase (E.C.

The referenced patents, patent applications, and scientific literature referred to herein are hereby incorporated by reference in their entirety. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

As used herein, the term "about" refers to an approximation of a stated value within an acceptable range. Preferably the range is +/−10% of the stated value.

Definite AD was diagnosed at autopsy using consensus neuropathological criteria (The NIA-Reagan Working Group. Consensus recommendations for the postmortem diagnosis of Alzheimer's disease. (1997) *Neurobiol. Aging*, 18:S1). The clinical definition for probable AD followed consensus recommendations (McKhann et al. (1984) *Neurology* 34:939) with impairment defined as psychometric performance falling at least 2 standard deviations (SD) below mean normative mean values in Learning/Memory [measured by the Wechsler Memory Scale-III Logical Memory Subtest, Hopkins Verbal Learning Test-Revised, or Brief Visual Memory Test-Revised, and 2 SD below normative mean on at least one test within the following cognitive domains: Attention/Information Processing [Verbal Sustained Attention Test, Symbol Digit Modalities Test, Wechsler Adult Intelligence Test-III Digit Span, Trails A Test, and Paced Auditory Serial-Addition Test (PASAT)], Orientation (Orientation questions), Language [Naming and Category Fluency, FAS Test], Executive Function [Wisconsin Card Sort Test and Trials B Test]. Subjects with MCI are defined as those without dementia but who show amnestic features including a memory complaint confirmed by an informant and a memory impairment measured at least 1.5 SD below normative mean values using the same testing battery as for AD.

The clinical definitions for HIV-related cognitive impairments followed consensus recommendation (Working Group of American Academy of Neurology AIDS Task Force (1992) *Neurology*, 41:778) with subjects showing no evidence for other etiologies. Measured impairment for HIV-associated dementia (HAD) fell 2.5 SD below normative means in one domain or 2 SD in at least two domains on any of the following tests: Learning/Memory, Language, Attention/Information Processing, Abstraction/Problem Solving, and Motor Abilities [Grooved Pegboard]. Subjects with mild cognitive-motor dysfunction (MCMD) are defined as those falling 1.5 SD below mean normative values in any test in at least two cognitive domains or 2.0 SD below mean values in a single domain.

As used herein, "loss of cognition" or variants thereof refer to a decline in at least one of information processing, attention, learning, information retrieval, and overall loss of intellectual function. Loss of cognition may be measured by any method known in the art, including, for example, Attention/Information Processing [Verbal Sustained Attention Test, Symbol Digit Modalities Test, Wechsler Adult Intelligence Test-III Digit Span, Trails A Test, and Paced Auditory Serial-Addition Test (PASAT)], Orientation (Orientation questions), Language [Naming and Category Fluency, FAS Test], Executive Function [Wisconsin Card Sort Test and Trials B Test], Learning/Memory, Abstraction/Problem Solving, Motor Abilities [Grooved Pegboard], and Hopkins Verbal tests. A subject at risk for loss of cognition has no measurable loss of cognition but has a greater chance for loss of cognition than the average population. For example, a first-degree relative of an Alzheimer's disease patient is at risk for loss of cognition.

As used herein, the term "contact" or "contacting" means bringing together, either directly or indirectly, a compound into physical proximity to a molecule of interest. Contacting may occur, for example, in any number of buffers, salts, solutions, or in a cell or cell extract.

The term "peptide bond" means a covalent amide linkage formed by loss of a molecule of water between the carboxyl group of one amino acid and the amino group of a second amino acid.

The term "saccharide" or "saccharide unit" includes oxidized, reduced or substituted saccharides. Saccharides of this invention include, but are not limited to, ribose, arabinose, xylose, lyxose, allose, altrose, glucose, mannose, fructose, gulose, idose, galactose, talose, ribulose, sorbose, tagatose, gluconic acid, glucuronic acid, glucaric acididuronic acid rhamnose, fucose, N-acetyl glucosamine, N-acetyl galactosamine, N-acetyl neuraminic acid, sialic acid, N-sulfated glucosamine (GlcNS), 2-sulfated iduronic acid (IdoA2S), derivatives of saccharides such as acetals, amines, and phosphorylated sugars, oligosaccharides, as well as open chain forms of various sugars, and the like. "Oligosaccharide" refers to a molecule having two or more saccharide units.

The term "purified", when used to describe the state of the neurotoxin of the invention, refers to a neurotoxin substantially free of other cellular material. "Substantially free" refers to at least about 60% or about 70%, more preferably at least about 80% or about 90%, and most preferably at least about 95%, about 98%, or about 100% free of other cellular materials.

The prodromic phase of pathology of neurodegenerative or neuro-inflammatory disease is defined herein as that stage in the disease during which the clinical manifestations of cognitive, behavioral, or social impairment have not yet reached a diagnostic threshold for MCI (amnesic features with memory testing 1.5 SD below normative mean) or AD (2 SD below normative means in memory and at least one other cognitive domain). By this definition, the prodromic phase would encompass, for example, the clinically-defined Cognitive Impairment, No Dementia (CIND) population (Toukko et al. (2001) *Int. Psychogeriatr., Supp.* 1:183-202), the at-risk asymptomatic population described by Hom ((1994) *J. Clin. Exp. Neurol.*, 16: 568-576), the Age-Associated Memory Impairment (AAMI, Goldman et al. (2001) *Alz. Dis. Assoc. Dis.*, 15: 72-79), the subclinical cohort of the Farmington study (Elias et al. (2000) *Arch. Neurol.* 57: 808-813) or a preclinical AD population defined identified at autopsy (Price et al. (2001) *Arch. Neurol.*, 58: 1395-1402). In general, all these groups show memory test values (verbal, episodic memory) at about 1 SD below normative mean scores adjusted for age, education, and ethnicity. Overall, populations at-risk for AD showed longitudinal declines at a rate of about 0.3 to 0.6 SD per year from normalized memory test scores tests.

The signaling cascade involved in the neurodegenerative diseases addressed by the present invention comprises events including (1) mononuclear phagocyte activation; (2) mononuclear phagocyte release of encephalotoxin; and (3) the toxic effect of encephalotoxins on neurons. Neurotoxicity of a mononuclear phagocyte induced by a mononuclear phagocyte activator may be inhibited or inactivated by an agent referred to herein as a neurotoxin inhibitor or inactivator.

A mononuclear phagocyte is an immune cell which has a single nucleus and the ability to engulf particles, also known as phagocytosis. Mononuclear phagocytes are found in blood and body tissues, including the central nervous system and brain, and include, for example, microglia cells, monocytes, macrophages, histiocytes, dendritic cells, precursor cells of microglia, precursor cells of monocytes, precursor cells of macrophages, microglia-like cell lines, macrophage-like cell lines, or cell lines modified to express microglia-like surface molecules that are active in accordance with the above definition of mononuclear phagocyte. A neuron as defined in accordance with the present invention includes a neuron and neuron-like cell, which is a cell modified to express a N-methyl-D-aspartate receptor which neuron exhibits neuronal activity under typical normal, non-diseased state, conditions.

Mononuclear phagocyte activation initiates a process that causes the release of neurotoxins. Mononuclear phagocyte activation is also referred to herein as immune activation, markers of which are any process that renders a mononuclear phagocyte more dynamic and characterized by activities such as and not limited to increased movement, phagocytosis, alterations in morphology, and the biosynthesis, expression, production, or secretion of molecules, such as protein, associated with membranes including complement, scavengers, Aβ, and blood cell antigens, histocompatibility antigens for example. Production of molecules includes enzymes involved in the biosynthesis of bioactive agents such as nitric oxide synthetase, superoxide dismutase, small molecules such as eicosanoids, cytokines, free radicals and nitric oxide. Release of factors includes proteases, apolipoproteins such as apolipoprotein E, and cytokines such as interleukin-1, tumor necrosis factor as well as other molecules such as encephalotoxin and hydrogen peroxide.

Mononuclear phagocyte neurotoxicity or neuron toxicity refers to a process that leads to the injury, destruction, or death of neurons, which is measured by loss of metabolic function, release of intracellular material, penetration of impermeant dyes, reduction of cell number measured by biochemical or histological methods. For example, changes in biochemical markers such as loss of neurofilaments or synaptophysin or release of lactate dehydrogenase, or other evidence of cell injury such as penetration of impermanent dyes, including fluorescent nuclear dyes and trypan blue. These and other strategies for identifying cell injury, destruction or death, or measuring neuron function, are known to one skilled in the art and are contemplated by the present invention.

Neurotoxin is defined herein as a substance that injures, damages, or kills a neuron while sparing other central nervous system cells such as glia, for example. A neurotoxin interacts with neurons in such a way as to disrupt neuron function and survival. The possible actions of a neurotoxin on neurons, also referred to herein as neuronal damage, include inhibition or disruption of normal cell metabolism, including metabolism of glucose, the production of ATP, and maintenance of ion gradients across cell membranes including $Na^+$, $Ca^{2+}$, and $K^+$ ion channels, the synthesis of proteins and nucleic acids, and mitochondrial respiration, and cell death.

Encephalotoxin as used herein refers to a class of neurotoxins having low molecular mass (<2000 daltons), heat stability, resistance to proteases, and loss of activity upon exposure to nitrous acid, N-sulfamidase, glucosamine-6-sulfatase, and heparin lyase I. Encephalotoxins comprise at least one GlcNS residue. An encephalotoxin preferably has a molecular weight between about 700 and 1,900 daltons. The encephalotoxin preferably has 4 to 8 saccharide residues.

Encephalotoxin inactivators or inhibitors are agents which inactivate neurotoxin or inhibit the effects of neurotoxins that are released from activated mononuclear phagocytes. For purposes of the present invention, inhibit, inhibition, inactivate, inactivation, and variations thereof are used synonymously with reduce, suppress, retard, slow, and suspend. Inactivation or inhibition also refers to complete inhibition of the neurotoxin cascade such that the cascade is arrested, stopped, or blocked. Encephalotoxin inactivation includes reduction of neurotoxic activity by about 10%, 20%, 50%, more preferably about 80%, 90%, or 95%, and most preferably about 98%, 99%, or 100%. By way of example, a compound is an encephalotoxin inactivator if it reduces the neurotoxic activity of the encephalotoxin or increases neuron survival such that neurons otherwise at risk of damage upon exposure to the encephalotoxin are not damaged in the presence of the encephalotoxin and the compound. Preferably, more than about 10%, 20%, or 50% of the neurons at risk are not damaged by the encephalotoxin in the presence of the encephalotoxin inactivator. Even more preferably, about 80%, 90%, or 95%, and most preferably, about 98%, 99%, or 100% of the neurons at risk are not damaged by the encephalotoxin in the presence of the encephalotoxin inactivator. Preferable encephalotoxin inactivators of the invention include heparin lyase I, N-sulfaminidase, glucosamine-6-sulfatase, and nitrous acid. Nitrous acid preferably has a pH of about 1.5. More preferably, exposure to nitrous acid occurs at room temperature.

An effective amount of a mononuclear phagocyte and an activator is the amount of each normally resulting in an event in the cascade, but for the addition of an encephalotoxin inactivator. An effective amount will be known to a skilled artisan in view of the present disclosure and will vary depending on the use of a mononuclear phagocyte, neuron, activator or components, and the mammalian origin of the cells.

In vitro neurotoxicity assays of the invention detect the presence of encephalotoxin and inactivation thereof and employ cultures of neurons or neuron-like cell lines which have been modified to express N-methyl-D-aspartate receptors. The presence of neurotoxic activity, or a measure of neuron function or measure of neuron survival, will be determined by reduction in cell number, changes in biochemical markers such as loss of cell metabolic function, release of intracellular material, penetration of impermeant dyes, such as and not limited to fluorescent nuclear dyes and trypan blue, loss of neurofilament or synaptophysin, release of lactate dehydrogenase, or other evidence of cell injury. Other methods of measuring neuron function include detecting the inhibition of normal cell metabolism including the disruption of glucose metabolism, ATP production, ion gradient maintenance across cell membranes, and protein synthesis, nucleic acid synthesis, and mitochondrial respiration. Reductions in an inflammatory marker or injury to a neuron by a test biological sample may be compared to a control. These and other strategies for identifying cell neurotoxicity or measuring neuron function, which may be displayed as cell injury, are known to one skilled in the art and are contemplated by the present invention.

Using the assay systems of the invention, it is possible to diagnose subjects at early, for example, pre-symptomatic or prodromic, stages of neurological disease. It is further possible, using the methods of the invention, to identify subjects or populations at risk for loss of cognition by detecting the encephalotoxin in a biological sample of a subject. The methods of the invention also allow monitoring of progression of neurological disease by detecting increases in encephalotoxin levels of a subject over time. The patients or subjects to be diagnosed in accordance with the present invention include and are not limited to mammals such as humans, primates such as and not limited to monkey, chimpanzee, and ape, rodents, such as and not limited to rat and mouse, guinea pig, dog, cat, rabbit, and pig. Biological samples in accordance with the methods of the invention include central nervous system tissue, such as brain or spinal cord tissue, or cerebrospinal fluid (CSF). The neurological diseases to be identified or monitored according to the invention include neurodegenerative and neuro-inflammatory diseases such as, but not limited to, Alzheimer's disease, Creutzfeldt-Jakob disease, HIV-1 associated dementia (HAD), Mild Cognitive Impairment, prion disease, minor cognitive/ motor dysfunction, acute stroke, acute trauma, neuro-AIDS, and immune-mediated brain inflammation.

The methods of the present invention include a neurotoxin assay of a biological sample of a patient, which can be used to diagnose a neurological disease or disorder or risk for loss of cognition in the subject. The methods of the present invention also may be used as an early detection method to identify individuals who are at risk for developing neurological diseases or disorders in view of their age, family history, early symptoms or other risk factors. For example, a biological sample, such as blood, spinal cord tissue, cerebrospinal fluid, or brain tissue, may be taken from a patient and evaluated with the encephalotoxin inactivators of the present invention, as described herein, to identify the presence of encephalotoxins in the patient or to identify patients who may suffer from a neurological disease. The patient's sample may be compared to a control to determine whether elevated levels of neurotoxins are present.

Similarly, the methods of the present invention employ the neurotoxin inactivators of the invention to monitor a patient's treatment or the rate of progression of a disease by determining the amount of neurotoxins that are present in the patient's system before and throughout treatment. The methods may also be used to monitor neurotoxin levels to allow for the adjustment of drug doses.

For example, the present invention provides methods for assaying the presence and level of encephalotoxin in a patient by contacting a biological sample of the patient with an encephalotoxin inactivator, such as heparin lyase I, N-sulfaminidase, glucosamine-6-sulfatase, or nitrous acid. Thereafter, the amount of inhibition in the presence of the inactivator is compared to a measured control. There is an increase of encephalotoxin in the subject when there is an increase in the encephalotoxin level compared to the control.

The present invention offers strategies for early detection of neurodegenerative disease or risk for loss of cognition, thereby allowing early intervention in disease progression. The following examples are illustrative only and are not intended to limit the scope of the invention.

EXAMPLES

Purification of Encephalotoxin

Encephalotoxins were isolated from cerebrospinal fluid by HPLC sieving chromatrophy (TSK-GEL G2500PWXL column; 7.8×300 mm from Tosoh Bioscience; Montgomeryville, Pa.) eluted with 2 M NaCl; by anion exchange HPLC (tandem ProPac PA1 columns 4×250 mm from Dionex Corp.; Sunnyvale, Calif.) with a linear gradient of 2 M NaCl over 180 min; or by adsorption chromatography (Oasis Cartridges, Waters) using the manufacturer's protocol.

Structural Characterization and Inactivation of Encephalotoxin

Figure 1B:
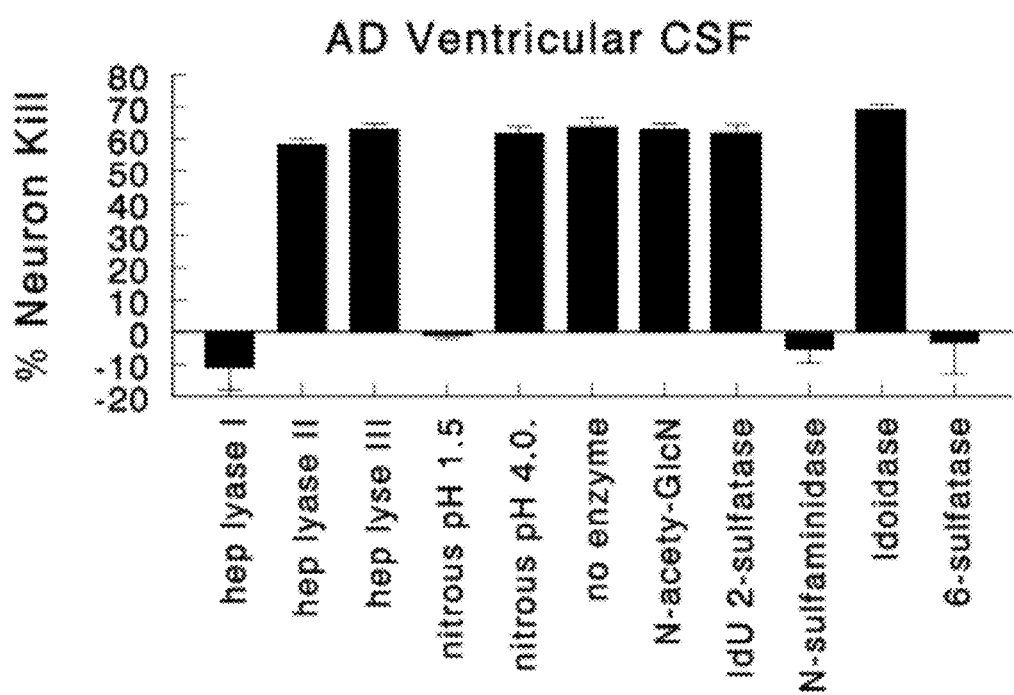
As shown in FIG. 1B, encephalotoxin found in ventricular CSF of AD brain was inactivated by nitrous acid pH 1.5, by heparin lyase I, and by sulfatases that cleave at O-6 and from GlcNS. As demonstrated in FIG. 1C, encephalotoxin recovered from lumbar CSF of subject with AD was inactivated by nitrous acid pH 1.5, by heparin lyase I, and by sulfatases that cleave at O-6 and from GlcNS.
Figure 1C:
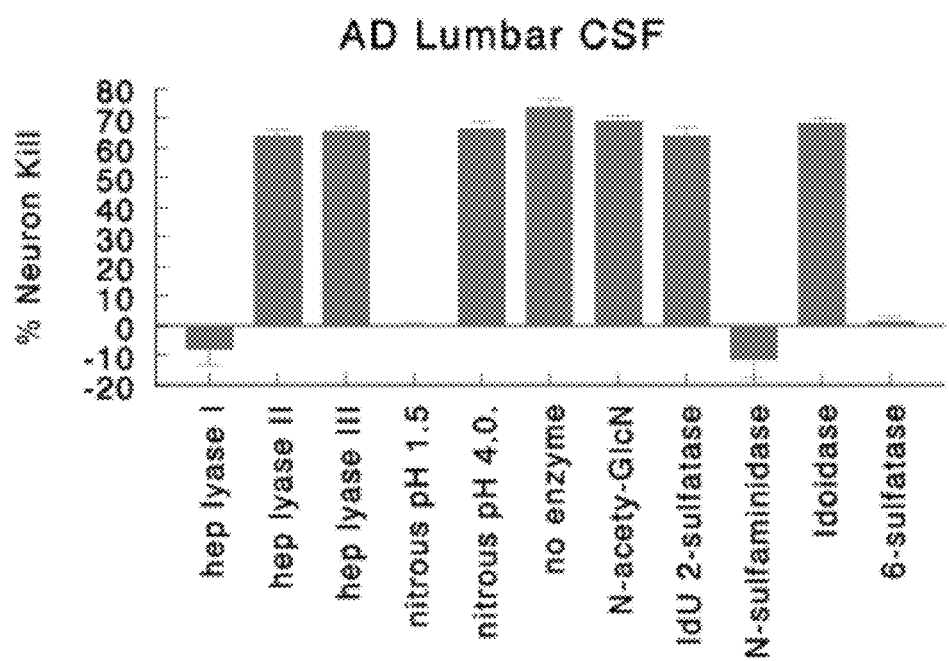
FIG. 1 illustrates inactivation of encephalotoxin by various methods specific for heparan sulfate and heparin.

Structural characterization and inactivation of encephalotoxin (isolated by organic extractions, gel filtration, and sequential C18 HPLC from Aβ-stimulated microglial cell line BV2) was performed by various nitrous acid cleavage protocols. Neurotoxic activity was eliminated by nitrous acid treatment at pH 1.5 but not by other acid treatments at pH 4.0 or with hydrazinolysis (FIG. 1). The results indicated that the internal structure of encephalotoxin contained at least one GlcNS residue. Encephalotoxin chemical structure was further examined by treatments with highly selective enzymes that attack heparin or heparan sulfate (HS) polymers. Traditionally, heparin lyase I acts primarily on heparin-containing GlcNS(1→4)IdoA2S sequences and heparin lyase III on HS primarily at a GlcNAc(1→4)IdoA or GlcNAc(1→4)GlcA sequence. (Generally, these enzymes require oligomers of at least 4 residues.) Finally, encephalotoxin was treated with sulfatases that are highly selective for O-sulfation sites at positions 2, 3, or 6 (found in HS and heparins) as well as N-sulfamidase which cleaves the N-sulfation site (FIG. 1). Heparin lyase I [GlNS(1→4)IdoA2S], but not heparin lyase III, inactivated encephalotoxin as did sulfatases that removed groups from O-6S and GlcNS. Additionally, chemical methods to modify terminal amines (acetylation, PFPA modification, etc.) suggested the presence of terminal amines, such as unsubstituted GlcN residues. Accordingly, encephalotoxin contains heparin-like oligosaccharides of at least 4 residues with GlcNS, IdoA2S, GlcN residues plus O-linked sulfation at position 6.

Figure 2:
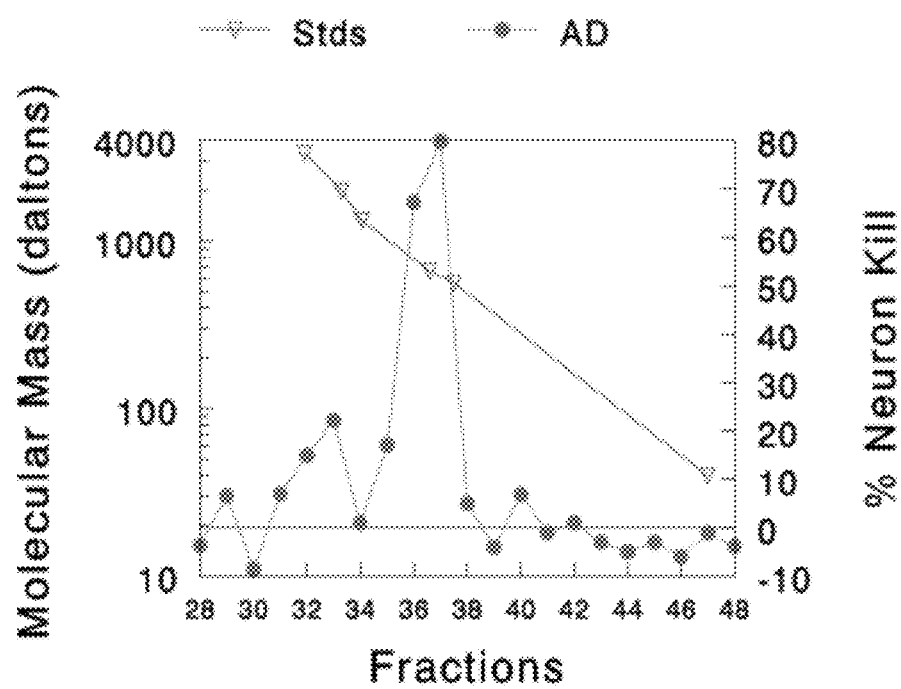
FIG. 2 illustrates the determination of molecular mass of encephalotoxin using a TSK-GW2500PXL with a linear sieving range from 300 to 3000 daltons. Commercially available heparan oligomers were used as standards. CSF samples (100 µl) from probable AD showed a minor peak and major peak of neurotoxic activity that range in size from about 700 to 1,900 daltons. These estimated molecular masses suggest that at least some forms of encephalotoxin comprise about 4 to 8 saccharide residues.

Molecular mass of the neurotoxin was estimated using a TSK-GW2500PXL with a linear sieving range from 300 to 3000 daltons. Commercially available heparan oligomers were used as standards. CSF samples (100 ul) from probable AD showed a minor peak and major peak of neurotoxic activity having low molecular weight ranging in size from about 700 to 1,900 daltons. These estimated molecular masses suggest oligosaccharides from about 4 to 8 residues in length (FIG. 2).

Neurotoxin Bioassay

Cultured neurons prepared from rat hippocampus were used in toxicity studies. These cultures consist of process-bearing neurons (10-20% of total cell population) atop a bed of astroglia (>70%) mixed with microglia (5-10%). In order to eliminate microglia, cultures were exposed to saporin coupled to acetylated LDL at 10 μg/ml for 18 hours. At the end of 72 hrs, the cultures were fixed in 3% paraformaldehyde at room temperature for 12 hours and immuno-stained by overnight incubation with a mixture of anti-neurofilament antibodies (SMI-311, 1:150; RT-97, 1:150; Sternberger Monoclonals, Inc.;) plus anti-MAP-2 (1:200; Boehringer Mannheim, 184959;) at 4° C. in the presence of 2% horse serum and 0.3% Triton X-100 to delineate both neuronal cell bodies and neurites. Immuno-labeled cells per field were scored at 200× magnification using fluorescence microscopy. Neuron killing was expressed as % mean survival expressed in terms of parallel untreated control cultures after scoring at least 8 randomly selected fields for each of 3 coverslips.

Figure 3:
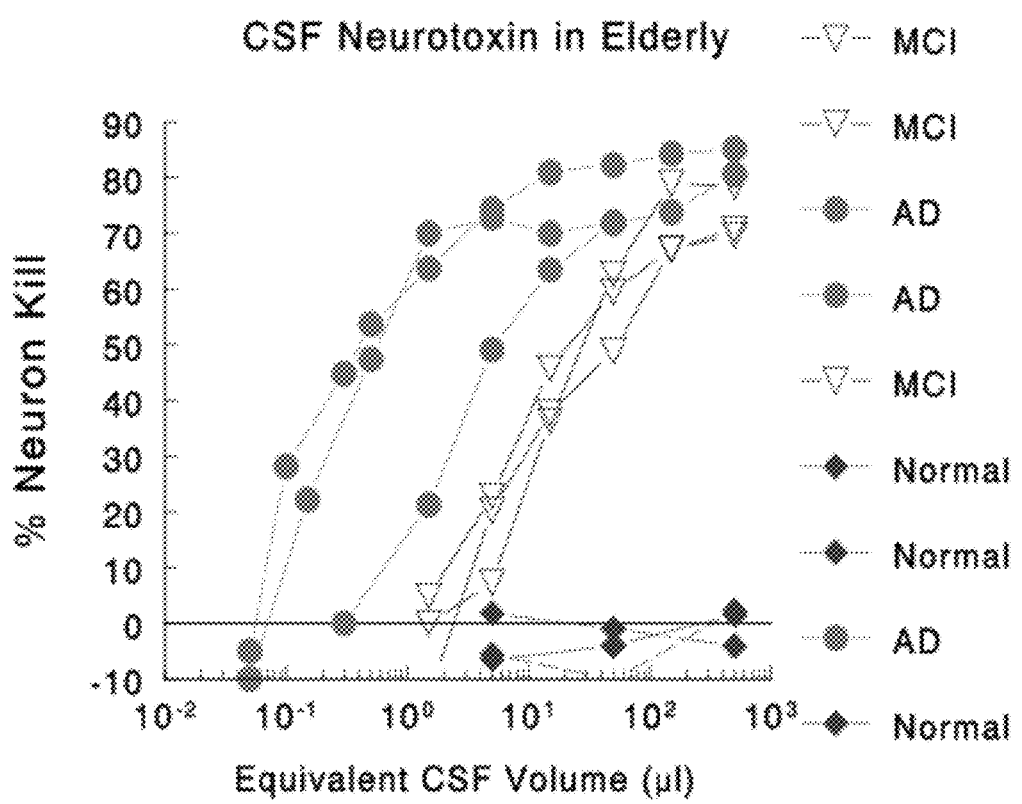
FIG. 3 shows dose response curves for encephalotoxin isolated from probable AD, MCI, and normal elderly subjects. Increasing amounts of toxin are found in those subjects with greater cognitive impairment.

1 ml of CSF was fractionated by adsorption chromatography, dried under vacuum, and reconstituted in artificial CSF comprising electrolytes, such as NaCl, and glucose. Increasing amounts of fractionated toxin (range 0.1 to 500 ul equivalents of original sample volume) were added to triplicate cultures. Results were plotted as volume vs. % neuron kill (with kill calculated as % loss of immuno-stained hippocampal neurons against untreated control cultures). Inactivation, for example, by heparin lyase I, N-sulfaminidase, glucosamine-6-sulfatase, or nitrous acid treatment, was used to confirm the presence of encephalotoxin for each CSF sample tested. As shown in FIG. 3, high levels of toxin (curves shifted to left) for AD, intermediate levels (curve shifted to right) for MCI, and toxin-free (flat line) profiles were noted for samples taken from disease controls. In order to compare different populations, a CSF Neurotoxicity Index was developed to assign scores that reflect level of neurotoxin. This index was calculated as an $ED_{50}$ (the equivalent CSF volume that yields 50% of the maximal level of neuron killing) Using this measurement, high neurotoxin levels have low Index scores; for example, high toxin concentrations have low Index scores of about 1, intermediate levels at about 5 to 100, and normal elderly show values of 1000.

Encephalotoxin Chemical Assay

Figure 4A:
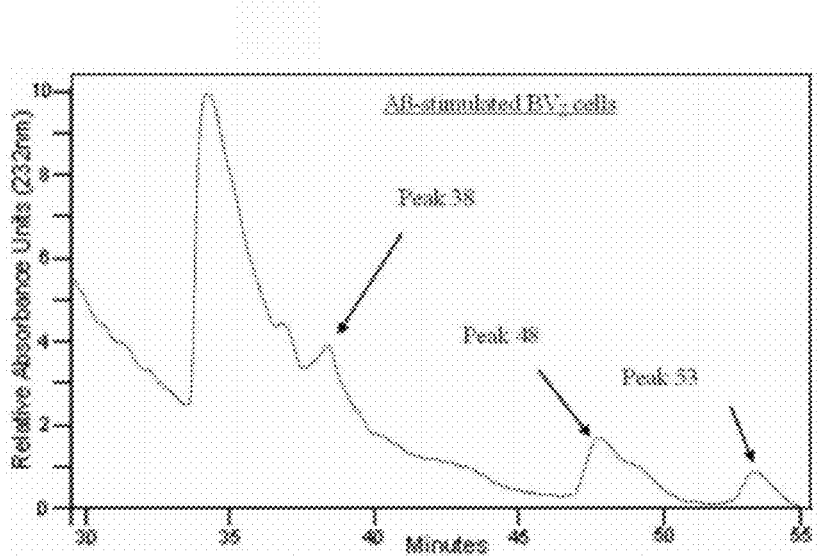
FIG. 4A shows the results of anion-exchange HPLC (ProPAK PA1, 0.0 to 0.7 M NaCl, UV @ 232 nm) separation of encephalotoxin from microglial BV2 cells stimulated with Aβ1-42. Three peaks (PEAK 38, 48, and 53) corresponding to the encephalotoxin were detected. The encephalotoxin of PEAKS 38, 48, and 53 was 1) sensitive to heparin lyase I, 2) sensitive to nitrous acid pH 1.5 and 3) toxic to hippocampal neurons (data not shown). As demonstrated in FIG. 4B, these same peaks were absent from conditioned media recovered from control BV2 cells that were not exposed to Aβ1-42.
Figure 4B:
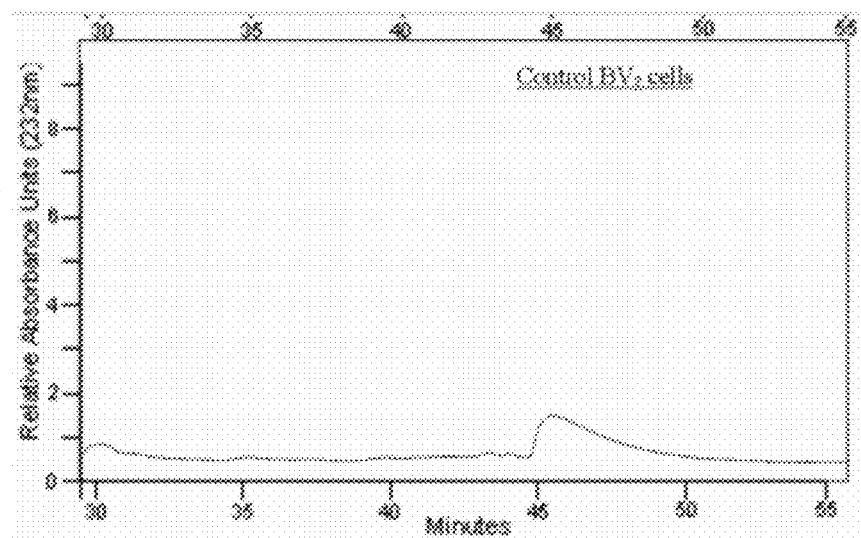

Anion-exchange HPLC conditions for the detection of encephalotoxin were established (0.0-0.7 m NaCl gradient; ProPAK PA-1 column; 232 nm UV monitoring). The microglial cell line BV2 was exposed to human Aβ1-42 for 48 hr and the conditioned media fractioned by adsorption chromatography. Three biologically-active peaks (PEAKs 38, 48, and 53) were recovered that corresponded to 3 peaks detected by 232 nm (FIG. 4A). All 3 peaks were sensitive to nitrous acid pH 1.5 and to heparin lyase I (data not shown). Importantly, none of these peaks were recovered from control cultures of unstimulated BV2 cells (FIG. 4B).

Encephalotoxin as CSF Biomarker for Neurodegenerative Disease

Figure 5A:
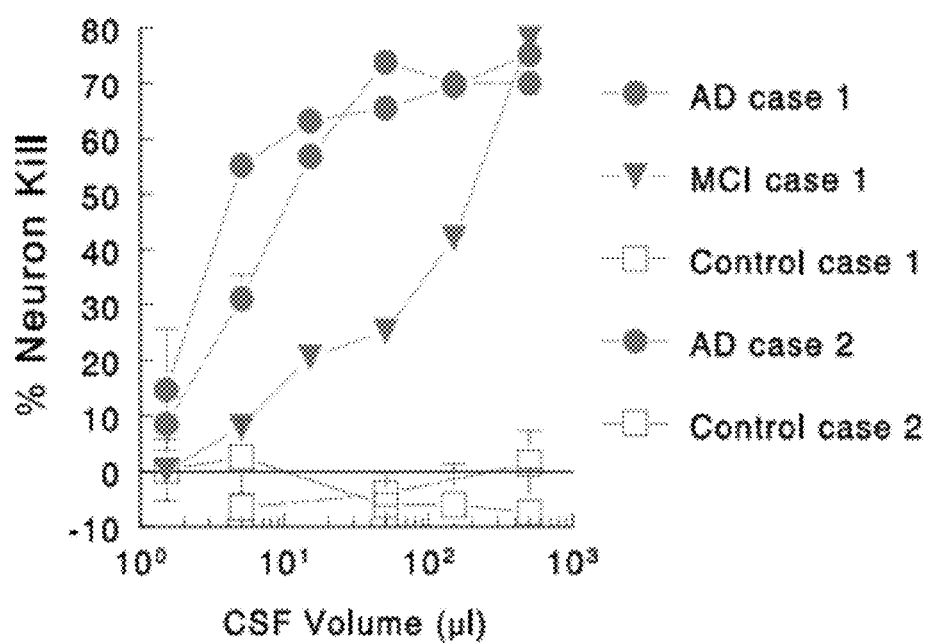
FIG. 5A illustrates the presence of encephalotoxin in ventricular and lumbar CSF recovered from autopsy cases.
Figure 5B:
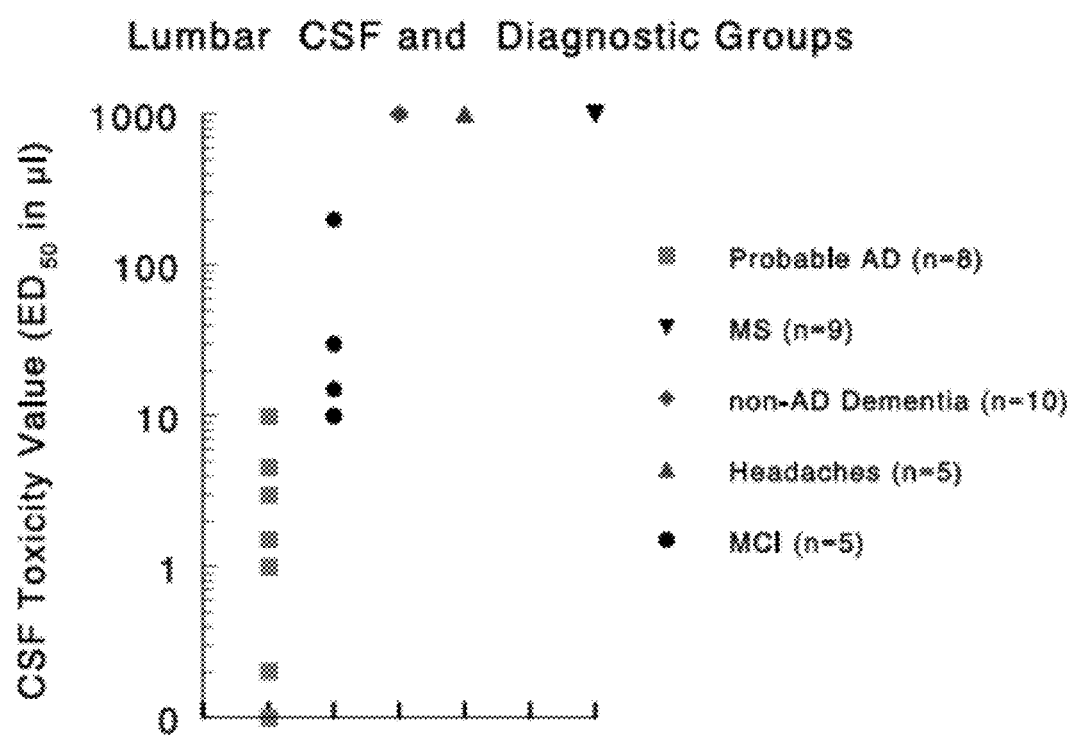
FIG. 5B illustrates the presence of encephalotoxin in ventricular and lumbar CSF recovered from living subjects. Data are expressed in terms of CSF volumes required to elicit death of cultured hippocampal neurons. As shown in the dose response curves (FIG. 5A), small volumes of high toxin concentrations shift curves to the left, as found in those subjects with definite AD (diagnosis confirmed by autopsy). These data can also be expressed as $ED_{50}$s (volumes of CSF required to give 50% maximal killing) As shown in FIG. 5B, a similar pattern was found in those subjects with probable AD (clinical diagnosis) who have small $ED_{50}$s (0.1 to 10 µl), followed by those in the MCI group with moderate values (10 to 200 µl). Importantly, various other diagnostic groups showed no detectable encephalotoxin ($ED_{50}$s>1000 µl).
Figure 6A:
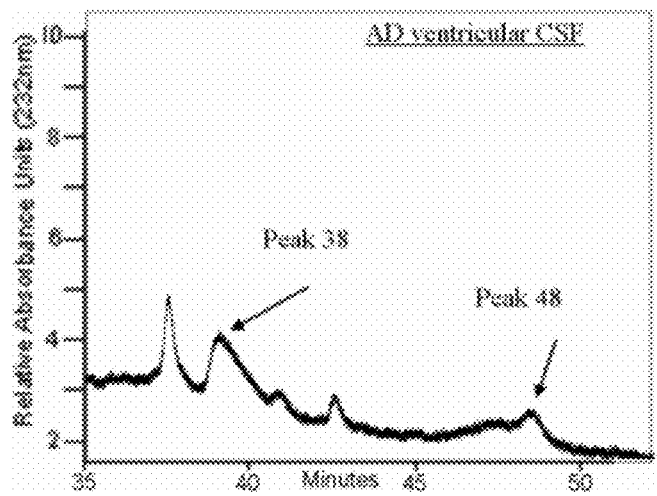
FIG. 6 shows PEAKs 38, 48, and 53 in CSF of AD (Panels A,B) and MCI (C), but not in normal elderly control (D) in anion exchange HPLC. These peaks were heparin lyase I sensitive (data not shown).
As shown in FIG. 6E, bioassays of these HPLC fractions confirm the same peaks are neurotoxic.
Figure 6B:
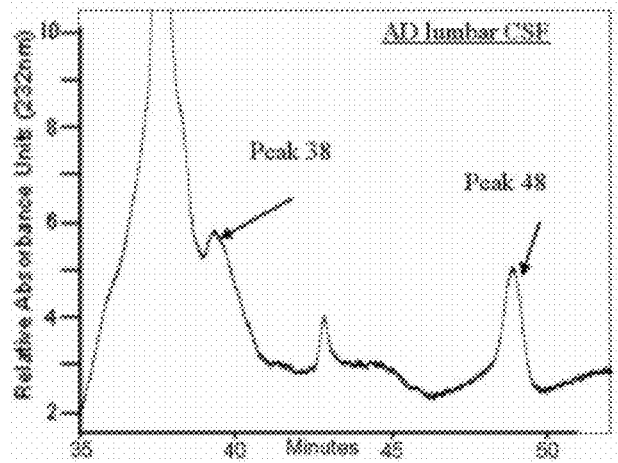
Figure 6C:
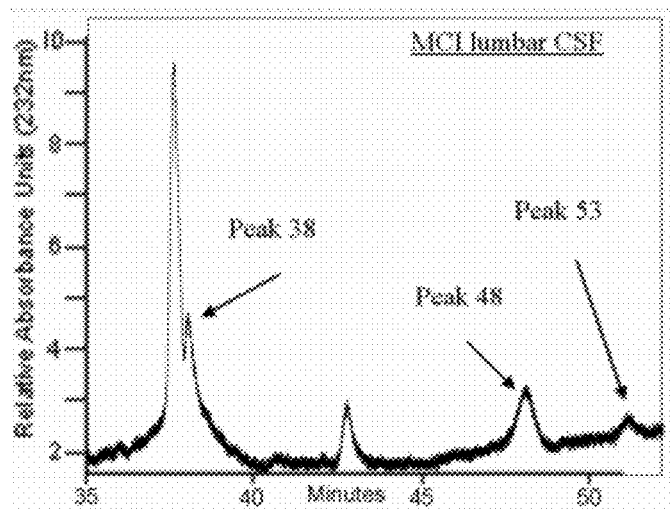
Figure 6D:
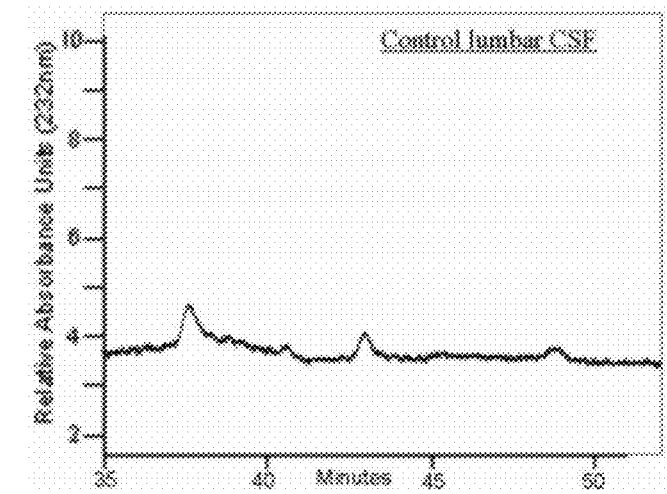
Figure 6E:
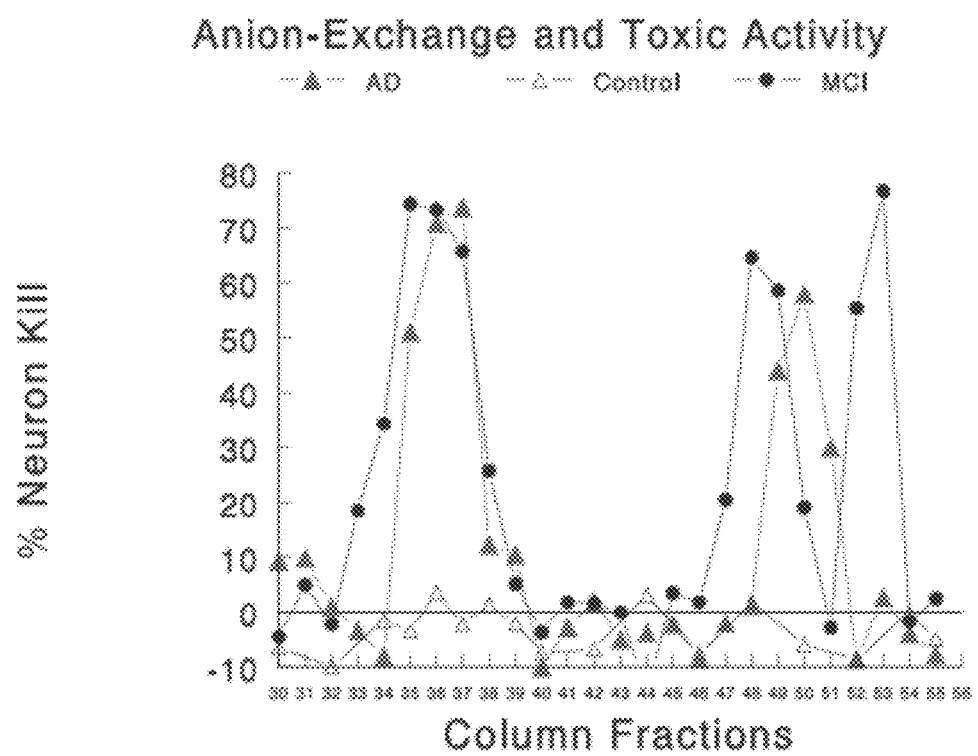

Using ventricular CSF from rapid autopsy cases, encephalotoxin was determined to be present in high concentrations in all CSFs from AD cases (confirmed by pathology), but not in cases from age-matched normals or ALS (FIG. 5). Importantly, lumbar CSF taken from subjects with a clinical diagnosis of probable AD also showed a striking pattern, with very high Encephalotoxin concentrations measured as $ED_{50}$s of between 0.1 to 5 μl.

A research protocol was established to evaluate samples not only from elderly subjects with cognitive impairment, but also from other groups seen by our clinic neurologists. The latter populations consisted of various diagnostic categories, with the largest groups suffering from headache variants, multiple sclerosis, or non-AD dementia (vascular, trauma). [Neurotoxin assays on these latter populations were performed with subject consent on remnant aliquots of CSF acquired for other clinical indications.] Data obtained thus far from subjects show that all patients with probable AD have high levels of neurotoxin, with $ED_{50}$s for equivalent CSF volumes ranging from 0.5 to 15 µl (note that lower $ED_{50}$ volumes indicate higher toxin concentrations); elderly subjects with MCI had $ED_{50}$ of between 50 and 200 µl. The non-parametric Kruskal-Wallis one-way ANOVA for ranks showed neurotoxin levels significantly differed (as measured by $ED_{50}$s) among tested disease groups (probable AD, MCI, non-AD dementia, headache, and MS; p=0.000001). The Kruskal-Wallis multiple-comparison test showed that both AD and MCI neurotoxin levels were significantly greater than these levels found in MS, headache, or non-AD dementia (p<0.02 for all comparisons).

Overall, these observations revealed several important trends. First, subjects with probable AD had the highest toxin concentrations, falling within a narrow range, similar to that of ventricular CSF from AD autopsy cases. Second, severe cognitive impairment or dementia secondary to non-inflammatory mechanisms (vascular, post-trauma) did not show detectable amounts of encephalotoxin in the CSF. [While neurotoxin can be found in tissues damaged acutely after stroke or trauma, these neurotoxin levels dissipate as the acute inflammatory response dissipates (about 3 to 7 days post injury; Giulian et al. (1990) *Ann. Neurol.*, 27: 33-42; Giulian et al. (1993) *Stroke*, 24: 84-93; Giulian (1993) *Glia*, 7: 102-110)]. And third, there appeared to be a trend of MCI subjects showing significant amounts of encephalotoxin, but only 1/10 to 1/100 as much total toxic activity as found in AD CSFs (FIG. 5).

To determine whether oligosaccharides associated with encephalotoxin were also found in human CSF, encephalotoxin was isolated from CSF by adsorption chromatography and treated with the same heparin lyases, nitrous acid treatments, and sulfatases as used for microglia culture media. Ventricular CSF from AD cases and lumbar CSF from probable AD subjects demonstrated the same inactivation profiles (FIG. 1), indicating that encephalotoxin in human disease contained heparin-like oligomers. Confirmation of the presence of such neurotoxic oligosaccharides came from anion-exchange HPLC, showing the presence of a neurotoxic PEAK 38 recovered from microglial encephalotoxin fractions. There were similarities between the CSF samples from AD and MCI by anion-exchange profiles (PEAKS 38 and 48) with an additional PEAK 53 in the MCI group (FIG. 6) as noted in microglial cultures (FIG. 4).

Figure 7A:
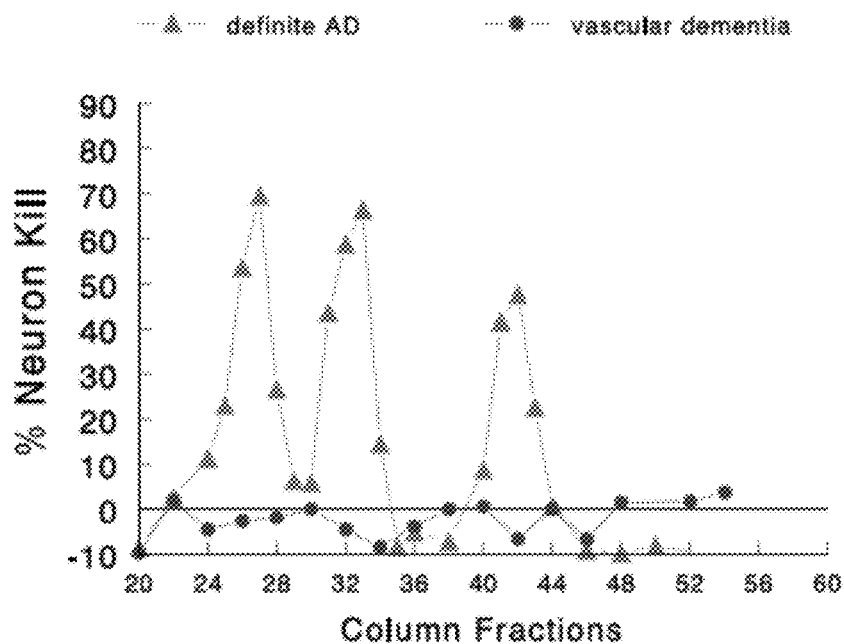
FIG. 7 shows that, in anion-exchange HPLC (linear gradient of 0 to 2.0 M NaCl over 90 min), 3 discrete peaks of neurotoxic activity are found in 100 µl of CSF from definite AD (FIG. 7A), probable AD (FIG. 7B), and HAD (FIG. 7C). No toxic activity is recovered from vascular dementia (FIG. 7A). Heparin lyase I and N-sulfaminidase, but not heparin lyase II, eliminate all toxin peaks.
Figure 7B:
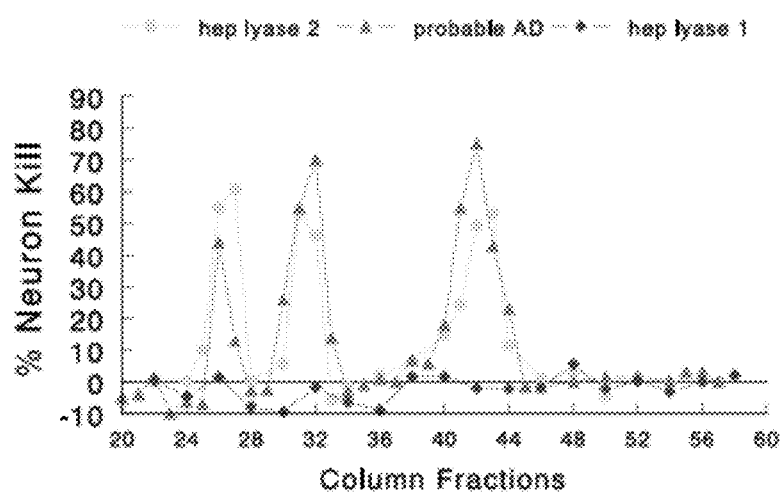
Figure 7C:
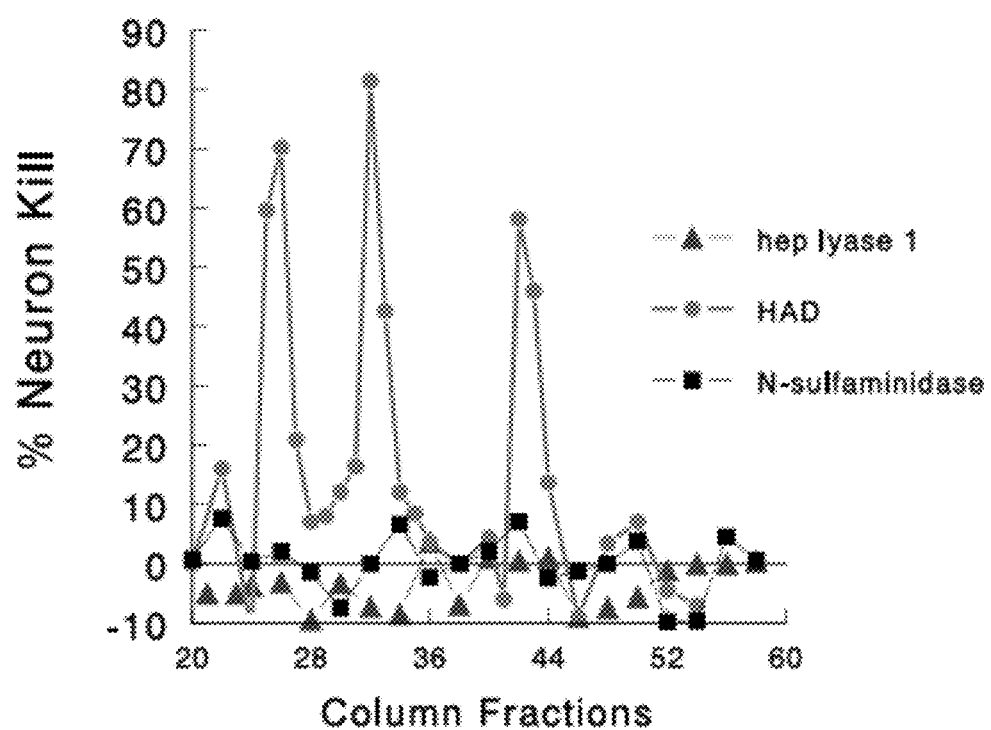

HPLC-profiles for ventricular cerebrospinal fluid of cases of definite AD were nearly identical to lumbar fluid samples from volunteers with probable AD (FIG. 7B) and from those with HAD (FIG. 7C). Enzymatic treatments by heparin lyase I and by N-sulfamindase eliminated all these peaks of neurotoxicity. Neuron-killing activity recovered by anion-exchange HPLC was insensitive to heparin lyase II (FIG. 7B), proteases, or heparin lyase III treatments (data not shown).

In order to survey the prevalence of neurotoxin production in neurological disorders, the cerebrospinal fluid of subjects from various disease populations was examined. Neurotoxin concentrations, expressed as CSF Neurotoxicity Index scores [expressed as equivalent volume of CSF which yields 50% of a total neuron killing effect in a standardized rat hippocampal culture assay], show that only those subjects with definite AD (postmortem diagnosis; n=7) or HIV-1 infection (n=52) had detectable levels of CSF neurotoxin (FIG. 8A). Neurologic disorders that can elicit chronic reactive immune responses, such as multiple sclerosis (MS; n=20), amyotrophic lateral sclerosis (ALS; n=8), or neuropathies (n=14), had no CSF neurotoxin. Similarly, subjects with psychiatric illness (n=5), with headache (n=6), or a variety of other neurological diseases (n=21; including fungal meningitis and neurosyphilis) are free of detectable neurotoxin. And finally, CSF samples obtained from volunteers undergoing routine myelography (n=20) contained no neurotoxin activity.

Figure 8B:
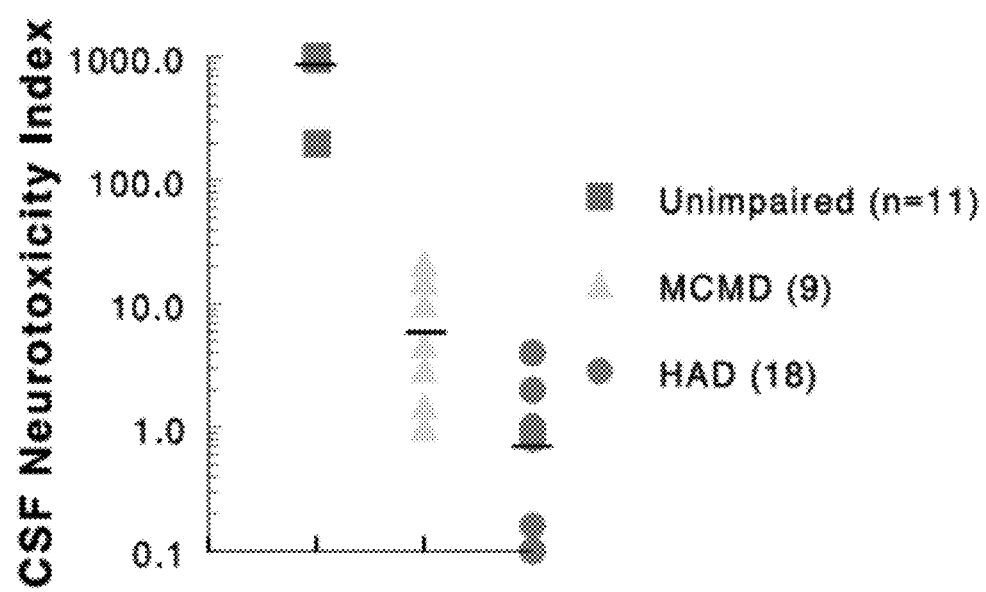
FIG. 8B compares CSF index scores with HIV-1(+) volunteers with no cognitive loss, mild cognitive motor dysfunction (MCMD), or HAD. Significant differences exist among MCMD and HAD, again supporting the pattern that more toxin is associated with greater degrees of cognitive impairment.
Figure 8D:
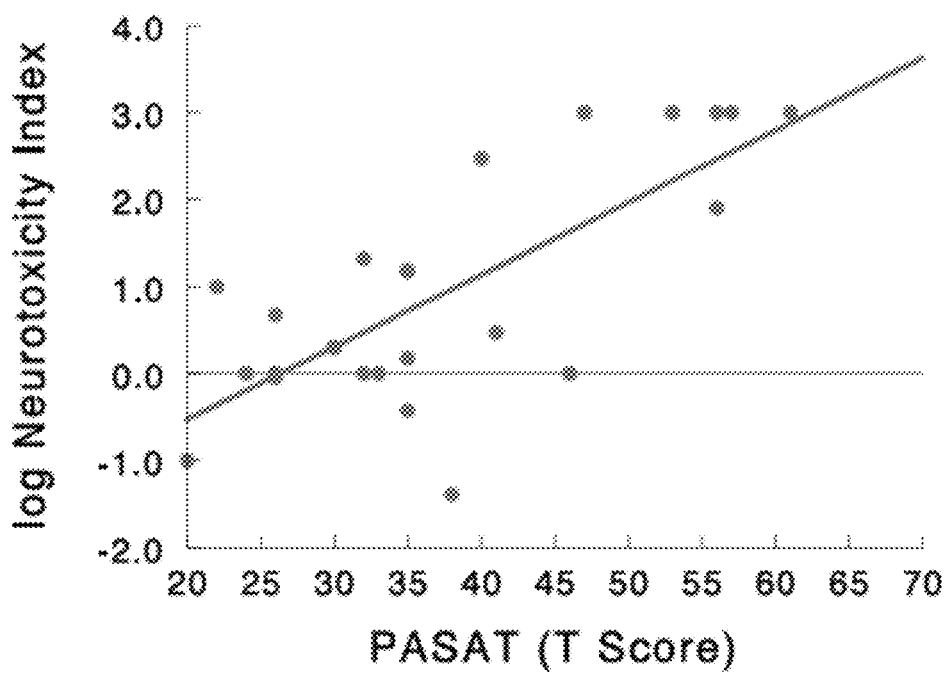
FIG. 8D compares Neurotoxicity Index values vs. T scores for the paced auditory serial-addition test (PASAT, a sensitive measure of information processing.) As shown, a significant linear relationship exists between CSF Neurotoxicity Index and this cognitive measure (n=26; p<0.0001; correlation coefficient=0.74).

Neurotoxicity Index values for CSF in cases of definite AD ranged between 1 and 10 whereas a broader distribution appeared for the HIV(+) population (0.1 to 1000). To investigate the wider distribution of neurotoxin levels for the HIV-1(+) cohort, 7 coded lumbar CSF samples from the HIV-1(+) volunteers who had undergone extensive medical, neurological, and neuropsychological evaluations were obtained through the Texas unit of the National Neuro-AIDS Tissue Consortium (Morello et al. (2001) *Neuropath. Appl. Neurobiol.*, 27:326-335). Neurotoxins are detected in those subjects with cognitive dysfunction (n=4) but not in those found to have normal cognition (n=3; Fisher's Exact Test, p=0.028). Low CSF Neurotoxicity Index scores were detected in HIV (+) subjects with HAD (range from 0.1 to 4.0); high Index scores were detected in HIV(+) subjects with little or no cognitive impairment (all >200), and intermediate Index scores (1.0 to 21.0) were associated with HIV(+) subjects identified with mild cognitive-motor disorder (MCMD; Working Group of American Academy of Neurobiology AIDS Task Force (1992) *Neurology*, 41:778; FIG. 8B). Significant differences between MCMD (median 7.3; mean+/−SE, 9.0+/−2.7; n=8) and HAD (0.1 median; 0.8+/−0.3; n=14) for Index values show a high confidence level (p=0.0001; Kruskal Wallis). The separation between HIV-1(+) subjects with MCMD group and those without cognitive impairment (median 1000.0; mean900+/−99.7 µl; n=8) is also significant (p=0.001). The degree of HIV injury to the CNS reflects levels of CSF neurotoxin, implying causal relationships among cognitive impairment, stage of brain pathology, and the production of neuron poisons.

In order to determine whether neurotoxin levels also reflect cognitive decline in the aged population, CSF was obtained from elderly volunteers with Mild Cognitive Impairment of the amnestic type (MCI; objective memory deficit, but without dementia; Bischkopf et al. (2002) *Acta Psychiatr. Scand.*, 106:403-414; n=6), a condition of impaired memory thought to reflect an early stage of AD (DeKosky et al. (2003) *Science*, 302:830). Comparison of subjects with MCI to elderly volunteers serving as controls (>70 years old and free of memory complaints; n=8) showed marked differences between the groups (FIG. 8C). The Neurotoxicity Index scores for MCI ranges from about 7 to 20 (median 10.0; mean 11.5+/−1.6; n=6) and are significantly lower than those measured for elderly controls (all >1000; n=8; Kruskal-Wallis; p=0.0005). Index scores for volunteers with probable AD (defined by clinical criteria) show a range of values from 0.1 to 10 (median 1.7, mean 3.0+/−0.8; n=21). Probable AD and MCI values are also significantly different (p=0.0111; Kruskal-Wallis), further evidencing an association between levels of CSF encephalotoxin and stage of brain pathology underlying cognitive dysfunction. Importantly, other forms of dementia lacking chronic brain inflammation, such as those secondary to trauma, alcoholism, or vascular injury, produce little or no detectable CSF neurotoxin (median 1000; mean 933.0+/−66.6; n=12). These observations are in agreement with CSF encephalotoxin values found in autopsy-confirmed cases for definite AD (FIG. 8A) and for vascular dementia (FIG. 8A).

In order to classify groups according to CSF neurotoxin concentrations, discriminant analyses were applied to three diagnostic categories for HIV(+) subjects and three categories for the elderly. As shown in Table 1, the CSF Neurotoxicity Index accurately predicts which HIV(+) volunteers will have little or no impairment in cognition (cut-off >100) from among those groups with MCMD (1-100) or HAD (<1). Similarly, the Index correctly separates subjects with non-Alzheimer's dementia (cut-off >100) from the elderly with MCI or AD. A cut-off value of >100 also predicts with 100% accuracy those elderly without memory complaints (see FIG. 8C).

TABLE 1

Cut-off Values for CSF Neurotoxicity Index According to Disease Category

A.

| Diagnostic Group | Neurotoxicity Cut-off Values | | |
|---|---|---|---|
| | >100 | 1-100 | <1 |
| HIV (+) unimpaired (n = 11) | 100% | 0% | 0% |
| Mild Cognitive Motor Dysfunction (MCMD) (n = 9) | 0% | 100% | 0% |
| HAD (n = 14) | 0% | 21% | 79% |

B.

| Diagnostic Group | Neurotoxicity Cut-off Values | | |
|---|---|---|---|
| | >100 | >4-100 | <4 |
| Non-AD dementia (n = 20) | 100% | 0% | 0% |
| MCI (n = 6) | 0% | 100% | 0% |
| AD (n = 20) | 0% | 33% | 67% |

CSF Encephalotoxin as a Biomarker for Progression of Disease Pathology

Data from 164 subjects showed that all patients with AD have high levels of neurotoxin in the CSF with $ED_{50}$s for equivalent CSF volumes ranging from 0.5 to 15 µl. Elderly subjects with mild cognitive impairment had levels between 50 and 200 µl. Subjects with various other neurological disorders, including neurodegenerative diseases, had no detectable toxicity ($ED_{50}$>1000 µl); vascular and post-trauma non-AD dementia also had no toxic activity. HIV-1 (+) subjects demonstrated a wide range of toxin concentrations ($ED_{50}$s ranging from 0.6 µl to >1000 µl).

CSF from 40 HIV-1 (+) individuals was examined. The level of toxicity was associated with the degree of cognitive impairment. For example, HIV-1 (+) subjects with normal cognition showed $ED_{50}$s>1000 µl, while those with moderate to severe cognitive defects produced neurotoxin levels of 0.6 to 5 µl, similar to the range found for AD subjects with established dementia. HIV-1 (+) subjects with mild to moderate cognitive impairments had intermediary levels of CSF neurotoxin with $ED_{50}$s ranging from 10 to 300 µl.

Figure 9:
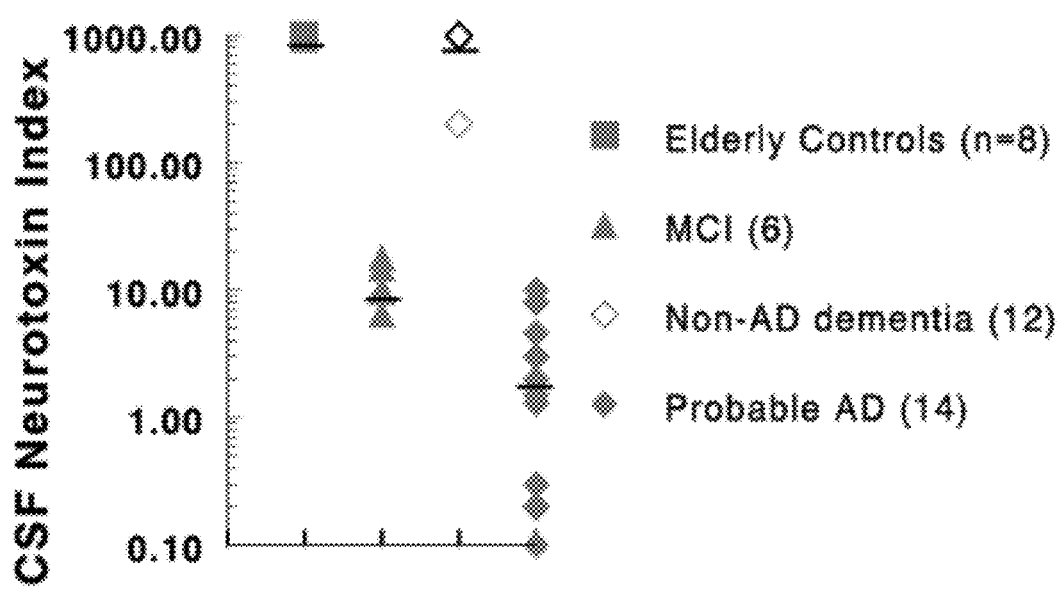
FIG. 9 shows a comparison of CSF Neurotoxicity Index scores of CSF from elderly subjects. Probable AD and MCI show significant toxin levels with an overlap in distribution of values. CSF neurotoxin levels clearly separate AD pathology from other categories common to the aged. (Bar=mean values.)
Figure 10:
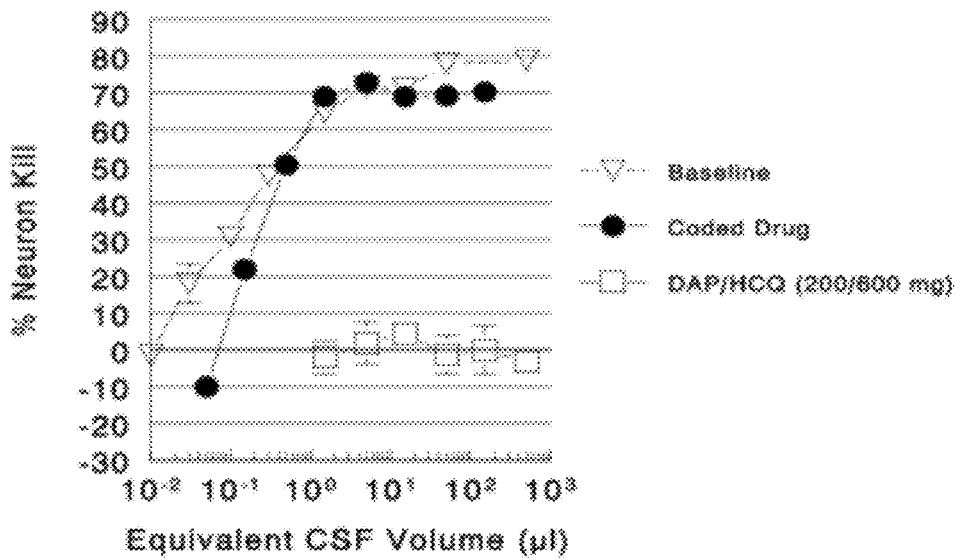
FIG. 10 shows two examples of drug effects upon CSF encephalotoxin levels. Single drug treatment (identity of drugs remains coded) failed to offer full suppression of toxin (i.e., shifted Index scores to a normal range of >100 as noted in Table 1) after a 6-week trial. In contrast, DAP/HCQ for 6 weeks provided complete inhibition of toxin production in all subjects tested to date (5 of 5).
Figure 10:
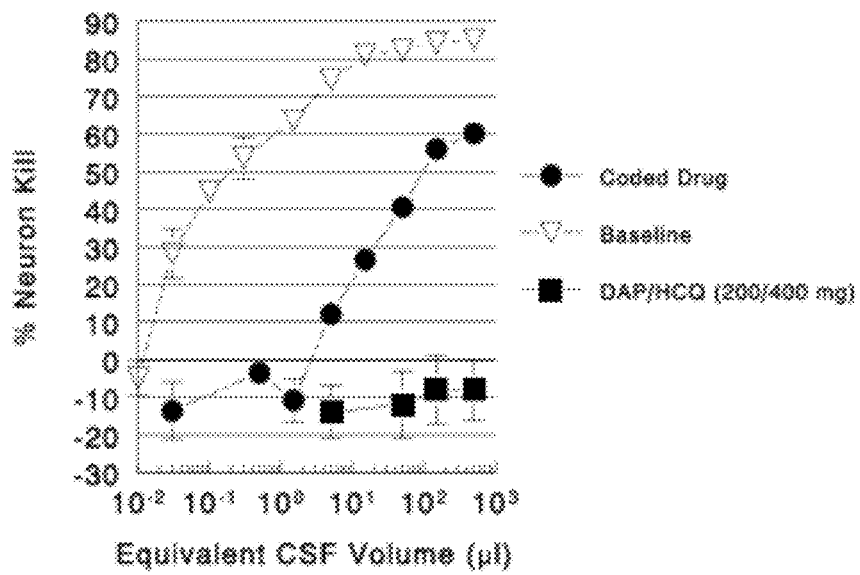

The Neurotoxicity Index in a variety of diagnostic groups was measured and compared against definite AD (n=7; defined by neuropathologic diagnosis using ventricular CSF obtained post mortem). As shown in FIG. 8A, there is a striking difference between AD and other diagnostic categories lacking measurable toxin (Index scores of 1000), thus evidencing the value of the Neurotoxicity Index across a broad population. Furthermore, as shown in FIG. 9, CSF encephalotoxin levels are clearly different among elderly without memory complaints or non-AD dementia (vascular, post traumatic, neurosyphillis) when compared to MCI (with amnestic features) or probable AD populations (using NINCDS-ADRDA diagnostic criteria). Discriminant analyses (Table 1B) established cut-off Neurotoxicity Index values for AD at <4 and for MCI at 4 to 100, providing the ability to correctly assign diagnosis based upon toxin values for MCI or probable AD against other groups. The underlying pathological process advances as a subject moves from a pre-symptomatic state to mild impairment (MCI with a 1.5 SD drop below norms of a standardized memory test) and then to a more advanced stage with dementia (AD with a 2 SD drop below norms in memory and at least one other domain). Earlier stages of disease prior to significant memory loss (stages before diagnosis of MCI) involve the neuron-damaging immune cascade which is detectable by the presence of CSF encephalotoxin. This subclinical stage is the prodromic phase of AD pathology.

Correlation between toxin levels and clinical manifestations of disease progression has been elucidated. MCI and mild AD subjects (MMSE>20; CDR<1) having CSF encephalotoxin were subjected to a detailed neuro-cognitive battery. Simple linear regression analyses were carried out comparing Neurotoxicity Index values with T scores from sets of standardized tests representing major cognitive domains. (T scores are normalized to 50 with 10 as SD; raw scores are adjusted for age, gender, ethnicity, and education level). As shown in Table 2, a highly significant correlation exists between Index scores and abnormal memory; that is, higher concentrations of toxin are found in those subjects with greater memory deficits while other cognitive domains (abstraction, language, processing speed) are not.

TABLE 2

| Cognitive Domain | p = | corr coef = |
|---|---|---|
| Executive Function | | |
| Wisconsin Card Sort | NS | |
| Trails B | NS | |
| Memory/Learning | | |
| Hopkins Verbal | 0.007 | 0.784 |
| WMS-III | 0.001 | 0.800 |
| Information Processing | | |
| digit symbol | NS | |
| symbol search | NS | |
| Trails A | NS | |
| Language | | |
| FAS | NS | |

Table 3 compares CSF Neurotoxin Index values and T scores for specific cognitive tests among HIV-1(+) volunteers (n=33). Confidence levels are based upon linear regression analyses and show that cognitive defects with domains of attention/information processing and learning/memory are closely associated with the amount of CSF encephalotoxin, while language and motor function are not. Prior to analysis, the Neurotoxicity Index was log transformed so that data would follow an approximate normal distribution.

TABLE 3

| Cognitive Domain | Test | Confidence Level (p=) | Correlation Coefficient |
|---|---|---|---|
| Abstraction/Problem Solving | | | |
| Visual Reasoning | Wisconsin Card Sort | 0.010 | 0.462 |
| Visual-Motor | Trails Making B | 0.003 | 0.514 |

TABLE 3-continued

| Cognitive Domain | Test | Confidence Level (p=) | Correlation Coefficient |
|---|---|---|---|
| Sequencing Language | | | |
| Verbal Fluency | FAS | NS | |
| Learning and Memory | | | |
| Auditory Word List | Hopkins Verbal Learning Test | 0.001 | 0.529 |
| Visual Simple Figures | Brief Visual Memory Test | 0.001 | 0.531 |
| Word Recall | Hopkins-Delayed Recall | 0.009 | 0.444 |
| Figure Recall | Brief Visual - Delayed Recall | 0.002 | 0.523 |
| Attention/Information Processing | | | |
| Auditory Series | PASAT | 0.000 | 0.735 |
| Number-Symbol Translation | WAIS III Digit Symbol | 0.014 | 0.427 |
| Visual Patterns | WAIS III Symbol Search | 0.000 | 0.574 |
| Visual-Motor Scanning | Trails Making A | 0.011 | 0.442 |
| Motor Abilities | | | |
| Psychomotor Speed/Dexterity | Grooved Pegboard | NS | |

Examine Effects of Suppressive Agents for Microglia Upon CSF Encephalotoxin Levels Use of encephalotoxin as a biomarker for monitoring drug treatment and disease progression was examined in a 6-week double-blind randomized study comparing several drugs against placebo with the primary endpoint as change in encephalotoxin levels in the CSF. Despite the masking of group assignments, a striking pattern was identified, as shown by representative data in FIG. 10. Although some subjects receiving coded drugs showed reduction in toxin levels by about 10-fold, such decreases did not shift subjects into the range of Index scores found among normal elderly (that is, Index scores remained below the MCI cut-off values of 100). These data suggested that none of the active drugs used in this trial were adequately dosed to provide complete neuroprotection. The persistence of significantly abnormal encephalotoxin concentrations made it unlikely that a single drug trial would alter the clinical course of AD.

A secondary endpoint was used to assess the ability of drug treatments to reduce Aβ-induced toxicity in cultured blood monocytes. It was found in animal studies that blood mononuclear phagocytes reflect brain microglial responses to Aβ. Accordingly, drug responses in cultures of blood monocytes having a baseline toxicity measure in enrolled subjects prior to drug treatments were examined after entry into the masked single drug trial. Study of 76 monocyte samples with measurement of Aβ-induced toxicity have shown the following:

1) in some cases a single drug (identity masked) completely suppress Aβ-activation of blood monocytes;
2) single drugs that suppress blood monocytes offer only a partial inhibition of CSF encephalotoxin levels;
3) ex vivo studies using blood monocytes from subjects without evidence of drug suppression demonstrated exquisite sensitivity to DAP/HCQ combinations at 1/10 doses.

The disclosure of each patent, patent application and publication cited or described in this document is hereby incorporated herein by reference, in its entirety.

Various modifications of the invention in addition to those shown and described herein will be apparent to one skilled in the art from the foregoing description. Such modifications are also intended to fall within the scope of the appended claims.

What is claimed:

1. A method of detecting chronic neuroinflammation of the brain associated with cognitive impairment and neurodegeneration in a subject comprising detecting an encephalotoxin in a biological sample of said subject, wherein said step of detecting comprises comparing light absorbance of said biological sample in the presence of an encephalotoxin inactivator to light absorbance of said biological sample in the absence of said encephalotoxin inactivator, an increased absorbance in the absence of said encephalotoxin inactivator being indicative of said chronic neuroinflammation, and the encephalotoxin being an oligosaccharide comprising at least one glucosamine having N-sulfation and O6-sulfation and lacking peptide bonds.

2. The method of claim 1 wherein said light absorbance is measured at a wavelength of 232 nanometers.

3. The method of claim 1 wherein the encephalotoxin inactivator is heparin lyase I, N-sulfaminidase, glucosamine-6-sulfatase, or nitrous acid solution.

4. The method of claim 1 wherein said chronic neuroinflammation is associated with HIV-1-associated dementia (HAD), neuro-AIDS, Creutzfeldt-Jakob Disease, Mild Cognitive Impairment, prion disease, minor cognitive/ motor dysfunction, or Alzheimer's disease (AD).

5. A method of monitoring treatment of chronic neuroinflammation of the brain associated with cognitive impairment and neurodegeneration in a subject comprising comparing encephalotoxin level in a first and second biological sample of said subject, wherein said first biological sample is taken from said subject at an earlier timepoint than said second biological sample, wherein said second biological sample is taken from said subject following treatment, and wherein said encephalotoxin level is measured by light absorbance of said biological sample, an increased absorbance of said second biological sample being indicative of progression of said chronic neuroinflammation, the encephalotoxin being an oligosaccharide comprising at least one glucosamine having N-sulfation and O6-sulfation; and said encephalotoxin lacking peptide bonds.

6. The method of claim 5 wherein said light absorbance is measured at a wavelength of 232 nanometers.

7. The method of claim 5 wherein said first biological sample is taken from said subject following said treatment.

8. The method of claim 5 wherein said chronic neuroinflammation is associated with HIV-1-associated dementia (HAD), neuro-AIDS, Creutzfeldt-Jakob Disease, Mild Cognitive Impairment, prion disease, minor cognitive/ motor dysfunction, acute stroke, acute trauma, or Alzheimer's disease (AD).

9. The method of claim 5 wherein said subject is human, primate, bovine, equine, canine, feline, porcine, or rodent.

10. The method of claim 5 wherein said subject is human.

11. A method of monitoring progression of chronic neuroinflammation of the brain associated with cognitive impairment and neurodegeneration in a subject comprising detecting an increase in encephalotoxin level in said subject over time, wherein said step of detecting comprises measuring an increased light absorbance of an encephalotoxin in a first biological sample of said subject relative to light absorbance of an encephalotoxin of a second biological sample of said subject, wherein said second biological sample is taken from said subject before said first biological sample, and wherein said encephalotoxin comprises an oligosaccharide comprising at least one glucosamine having N-sulfation and O6-sulfation, and lacks peptide bonds, said increased light absorbance being indicative of progression of said chronic neuroinflammation.

12. The method of claim 11 wherein said chronic neuroinflammation is associated with HIV-1-associated dementia (HAD), neuro-AIDS, Creutzfeldt-Jakob Disease, Mild Cognitive Impairment, prion disease, minor cognitive/motor dysfunction, or Alzheimer's disease (AD).

13. The method of claim 11 wherein said light absorbance is measured at a wavelength of 232 nanometers.

14. A method of detecting an encephalotoxin in a biological sample of a subject, comprising comparing light absorbance of said biological sample in the presence of an encephalotoxin inactivator to light absorbance of said biological sample in the absence of said encephalotoxin inactivator, an increased absorbance in the absence of said encephalotoxin inactivator being indicative of said encephalotoxin, the encephalotoxin being an oligosaccharide comprising at least one glucosamine having N-sulfation and O6-sulfation, and lacks peptide bonds.

15. The method of claim 14 wherein said light absorbance is measured at a wavelength of 232 nanometers.

16. The method of claim 14 wherein the encephalotoxin inactivator is heparin lyase I, N-sulfaminidase, glucosamine-6-sulfatase, or nitrous acid solution.

17. A method of detecting a neurological disease in a subject, said method comprising:
   determining a neurotoxicity index of cerebrospinal fluid of said subject, wherein the neurotoxicity index is equivalent to the volume in microliters of cerebrospinal fluid necessary to result in 50% killing of neurons in vitro relative to neuron survival in the presence of encephalotoxin inactivator-treated cerebrospinal fluid sample,
   wherein the encephalotoxin inactivator is heparin lyase I, N-sulfaminidase, glucosamine-6-sulfatase, or a nitrous acid solution, and
   wherein a neurotoxicity index of 100 or less is indicative of said neurological disease at a level associated with clinical diagnosis of disease.

18. A method for monitoring change of neurological disease in a subject, said method comprising:
   determining a neurotoxicity index of a first cerebrospinal fluid sample of said subject and a neurotoxicity index of a second cerebrospinal fluid sample of said subject, wherein the neurotoxicity index is a calculated value determined by a bioassay comprising
   1) contacting a cerebrospinal fluid sample of said subject with neurons in vitro, and
   2) comparing neuron survival in the presence of said cerebrospinal fluid sample to neuron survival in the presence of encephalotoxin inactivator-treated cerebrospinal fluid sample, wherein the encephalotoxin inactivator is heparin lyase I, N-sulfaminidase, glucosamine-6- sulfatase, or a nitrous acid solution
   and wherein the neurotoxicity index is equivalent to the volume of cerebrospinal fluid sample necessary to result in 50% killing of neurons relative to neuron survival in the presence of encephalotoxin inactivator-treated cerebrospinal fluid sample,
   wherein said second cerebrospinal fluid sample is taken at a later time point than said first cerebrospinal fluid sample,
   wherein a decrease in said neurotoxicity index of said second cerebrospinal fluid sample relative to said neurotoxicity index of said first cerebrospinal fluid sample is indicative of progression of said neurological disease, and
   wherein an increase in said neurotoxicity index of said second cerebrospinal fluid sample relative to said neurotoxicity index of said first cerebrospinal fluid sample is indicative of regression of said neuroinflammation.

19. The method of claim 18 wherein one of said cerebrospinal fluid samples is taken during the prodromic phase of said neurological disease.

20. A method of monitoring treatment of neurological disease in a subject, said method comprising:
   determining a neurotoxicity index of a first cerebrospinal fluid sample of said subject and a neurotoxicity index of a second cerebrospinal fluid sample of said subject, wherein the neurotoxicity index is a calculated value determined by a bioassay comprising
   1) contacting a cerebrospinal fluid sample of said subject with neurons in vitro, and
   2) comparing neuron survival in the presence of said cerebrospinal fluid sample to neuron survival in the presence of encephalotoxin inactivator-treated cerebrospinal fluid sample, wherein the encephalotoxin inactivator is heparin lyase I, N-sulfaminidase, glucosamine-6-sulfatase, or a nitrous acid solution,
   and wherein the neurotoxicity index is equivalent to the volume of cerebrospinal fluid sample necessary to result in 50% killing of neurons relative to neuron survival in the presence of encephalotoxin inactivator-treated cerebrospinal fluid sample,
   wherein said second cerebrospinal fluid sample is taken following said treatment and at a later time point than said first cerebrospinal fluid sample,
   wherein a decrease in said neurotoxicity index of said second cerebrospinal fluid sample relative to said neurotoxicity index of said first cerebrospinal fluid sample is indicative of progression of said neurological disease, and
   wherein an increase in said neurotoxicity index of said second cerebrospinal fluid sample relative to said neurotoxicity index of said first cerebrospinal fluid sample is indicative of successful treatment.

21. The method of claim 17, claim 18, or claim 20 wherein said neurological disease is HIV-I-associated dementia (HAD), neuro-AIDS, Creutzfeldt-Jakob Disease, Mild Cognitive Impairment, prion disease, minor cognitive/motor dysfunction, or Alzheimer's disease (AD) or the prodromic phase of HIV-I-associated dementia (HAD), neuro-AIDS, Creutzfeldt-Jakob Disease, Mild Cognitive Impairment, prion disease, minor cognitive/motor dysfunction, or Alzheimer's disease (AD).

22. A method of detecting an encephalotoxin in a biological sample of a subject comprising:
   A) contacting a biological sample of said subject with neurons, wherein said biological sample is cerebrospinal fluid, spinal cord tissue, or brain tissue, and B) comparing neuron survival in the presence of said biological sample treated with encephalotoxin inactivator relative to neuron survival in the presence of said biological sample not treated with said encephalotoxin inactivator, wherein a decrease in neuron survival in the absence of said encephalotoxin inactivator treatment relative to neuron survival in the presence of said encephalotoxin inactivator treatment is indicative of said encephalotoxin, and wherein the encephalotaxin inactivator is heparin lyase I, N-sulfaminidase, glucosamine-6-sulfatase, or a nitrous acid solution.

23. The method of claim 17, 18, 20, or 22 wherein said subject is human, primate, bovine, equine, canine, feline, porcine, or rodent.

* * * * *